US008076092B2

(12) United States Patent
Akhavan-Tafti

(10) Patent No.: US 8,076,092 B2
(45) Date of Patent: Dec. 13, 2011

(54) NONSEPARATION ASSAY METHODS

(75) Inventor: Hashem Akhavan-Tafti, Howell, MI (US)

(73) Assignee: Beckman Coulter, Inc., Brea, CA (US)

(*) Notice: Subject to any disclaimer, the term of this patent is extended or adjusted under 35 U.S.C. 154(b) by 0 days.

(21) Appl. No.: 13/084,303

(22) Filed: Apr. 11, 2011

(65) Prior Publication Data

US 2011/0269156 A1    Nov. 3, 2011

Related U.S. Application Data

(60) Continuation of application No. 12/885,763, filed on Sep. 20, 2010, now Pat. No. 7,923,214, which is a division of application No. 11/800,963, filed on May 8, 2007, now Pat. No. 7,799,534.

(60) Provisional application No. 60/798,839, filed on May 9, 2006.

(51) Int. Cl.
*G01N 33/53* (2006.01)
*G01N 31/00* (2006.01)

(52) U.S. Cl. ........ 435/7.21; 435/7.1; 436/501; 436/518; 422/50; 424/9.1

(58) Field of Classification Search ........................ None
See application file for complete search history.

(56) References Cited

U.S. PATENT DOCUMENTS

| | | | | |
|---|---|---|---|---|
| 6,406,913 | B1 * | 6/2002 | Ullman et al. | 435/41 |
| 7,799,534 | B2 * | 9/2010 | Akhavan-Tafti | 435/7.21 |
| 7,923,214 | B2 * | 4/2011 | Akhavan-Tafti | 435/7.21 |

* cited by examiner

*Primary Examiner* — Lisa Cook
(74) *Attorney, Agent, or Firm* — Richard S. Handley

(57) ABSTRACT

Assay methods are disclosed involving specific binding reactions which are simplified compared to known methods. A compound capable of producing chemiluminescence is immobilized on a solid support as is a member of a specific binding pair for capturing an analyte from a sample. An activator compound that activates the chemiluminescent compound and is conjugated to a specific binding pair member is added in excess along with the sample to the solid support. Addition of a trigger solution causes a chemiluminescent reaction at the sites where the activator conjugate has been specifically bound. The assay methods are termed non-separation assays because they do not require removal or separation of excess detection label (activator conjugate) prior to the detection step. The methods are applicable to various types of assays including immunoassays, receptor-ligand assays and nucleic acid hybridization assays.

24 Claims, 9 Drawing Sheets

NONSEPARATION ASSAY METHODS

CROSS-REFERENCE TO RELATED APPLICATION

The present application is a Continuation of U.S. patent application Ser. No. 12/888,763, filed on Sep. 20, 2010, which is a Divisional of U.S. patent application Ser. No. 11/800,963, filed May 8, 2007, now U.S. Pat. No. 7,799,534, which claims the benefit of priority to U.S. Provisional Patent Application Ser. No. 60/798,839, filed on May 9, 2006.

FIELD OF THE INVENTION

The present invention relates to novel assay methods involving specific binding reactions which are simplified compared to known methods. The assay methods are termed non-separation assays because they do not require removal or separation of excess detection label prior to the detection step. The methods are applicable to various types of assays including immunoassays, receptor-ligand assays and nucleic acid hybridization assays.

BACKGROUND OF THE INVENTION

A huge effort has been expended in the field of assay development, in particular in immunoassay development, to simplify the design of assays while preserving their essential benefits in sensitivity, dynamic range, robustness, broad applicability, and suitability to automation. One approach has been to devise so-called homogeneous assay formats where no separation of an added detectably labeled specific binding partner is used. This type of methodology relies on devising a detection principle that is either turned on or turned off as a result of the binding reaction. In contrast, heterogeneous assays formats rely on physical separation of bound and free detectably labeled specific binding partners before quantitation.

Numerous U.S. patents have been issued in the field of homogeneous enzyme immunoassay. Many exploit the antibody:antigen binding reaction to either activate or inhibit a label enzyme: U.S. Pat. Nos. 3,817,837; 3,852,157; 3,875,011; 3,966,556; 3,905,871; 4,065,354; 4,043,872; 4,040,907; 4,039,385; 4,046,636; 4,067,774; 4,191,613; 4,171,244; and 4,785,080. Other homogeneous immunoassays involve various methods of quenching fluorescence through antibodies or other fluorescent quenchers: U.S. Pat. Nos. 3,998,943; 3,996,345; 4,174,384; 4,161,515; 4,208,479; and 4,160,016. Still other U.S. patents in this field of assorted types of immunoassay include: U.S. Pat. Nos. 3,935,074; 4,130,462; and 4,193,983. U.S. Pat. No. 4,160,645 discloses an assay method using an electron transfer catalyst as a label. The catalyst (label) is deactivated by bonding to antibody.

Campbell et al., (Biochem. J., 216, 185-194 (1983)), discloses a detection method using energy transfer between a chemiluminescence donor coupled to an antigen (Ag-L) and a fluorescence acceptor coupled to an antibody (Ab-F) in a competitive assay format. Complexed antigen ultimately emits at the wavelength of the fluorescer, while free antigen emits at the characteristic wavelength of the chemiluminescence label. Subsequently, the light intensity is measured at two wavelengths and the ratio of the two signals is related to the amount of analyte in the sample.

Various other homogeneous immunoassays are known: Rubenstein, et al, U.S. Pat. No. 3,817,837 (Homogeneous Enzyme Immunoassay); Ullman, U.S. Pat. No. 3,996,345 (Fluorescence Quenching Homogenous Immunoassay); Maggio, U.S. Pat. No. 4,233,402 (Enzyme Channeling Homogeneous Enzyme Immunoassay); and Boguslaski, et al., Canadian Patent 1,082,577 (Hapten-Cofactor Homogeneous Enzyme Immunoassay).

U.S. Pat. No. 6,406,913 to Ullman discloses assay methods comprising treating a medium suspected of containing an analyte under conditions such that the analyte causes a photosensitizer and a chemiluminescent compound to come into close proximity. The photosensitizer generates singlet oxygen, which diffuses through solution to and activates the chemiluminescent compound when it is in close proximity. The activated chemiluminescent compound subsequently produces light. The amount of light produced is related to the amount of analyte in the medium. In one embodiment, at least one of the photosensitizer or the chemiluminescent compound is associated with a suspendible particle, and a specific binding pair member is bound thereto.

U.S. Pat. No. 5,516,636 to McCapra discloses assay methods comprising specific binding assays which utilize a sensitizer as a label. The sensitizer, when stimulated by radiation, electron transfer, electrolysis, electroluminescence or energy transfer, achieves an excited state, which (a) upon interaction with molecular oxygen produces singlet oxygen, or (b) upon interaction with a leucodye is reduced by oxygen to produce hydrogen peroxide. Either interaction with the excited sensitizer, with the addition of other reagents, produces a detectable signal.

U.S. Pat. No. 6,911,305 to Levison discloses a method of detecting polynucleotide analytes bound to a sensitizer or a sensitizer-labeled probe on a first film. The film is contacted with a second film having a chemiluminescent precursor component immobilized thereon; the precursor is capable of producing a triggerable chemiluminescent compound. The sensitizer is excited to produce singlet oxygen for reaction with the chemiluminescent precursor to form the triggerable chemiluminescent compound on said second film. Then the triggerable chemiluminescent compound is triggered to produce a detectable light signal on said second film.

U.S. Pat. Nos. 6,994,980 and 6,723,851 disclose methods for detecting an analyte using compounds that become deposited or bound to an analyte or the area surrounding the analyte after reaction with an enzyme. The enzyme can be supplied in the assay methods as a conjugate with a substance that specifically binds the analyte. The compound is supplied in free form for reaction with the enzyme, in one embodiment as a liquid composition. After the enzymatic reaction induced deposition, the deposited compound is detected by a nonenzymatic chemiluminescent reaction of an acridinium ester moiety contained within the molecule with hydrogen peroxide at alkaline pH. No enzymatic reaction occurs between bound enzyme and bound chemiluminescent compound.

Despite the considerable efforts made in devising homogeneous, or non-separation, assay formats, they still do not experience widespread commercial adoption. Heterogeneous assays are viewed as simpler to develop and mass-produce, albeit operationally more complex. In particular, the field of high volume clinical immunodiagnostics and the smaller field of clinical nucleic acid diagnostics are dominated by heterogeneous assay formats. Within this arena, test formats would be beneficial to the field that could simplify protocols, reduce complexity and improve compatibility with automation by removing unnecessary steps.

SUMMARY OF THE INVENTION

In one aspect, the present invention provides novel assay methods involving specific binding reactions, especially immunoassays, receptor assays and nucleic acid hybridization assays, which are simplified compared to known methods. The methods feature the use of an immobilized chemiluminescent compound and an activator compound conjugated to a specific binding partner for inducing a chemiluminescent reaction. Analyte-mediated co-localization of the chemiluminescent label compound and the activator conjugate causes the ensuing chemiluminescent reaction to take place only at the site of the bound analyte molecules. The presence of unbound, excess activator conjugate does not contribute to or interfere with the chemiluminescent reaction. As a result, the intensity of chemiluminescence emitted is proportional to the quantity of analyte. In one embodiment assays are simplified by eliminating separation and washing steps prior to the detection step and thus can be deemed non-separation assays.

DETAILED DESCRIPTION OF THE INVENTION

Definitions

Figure 1:
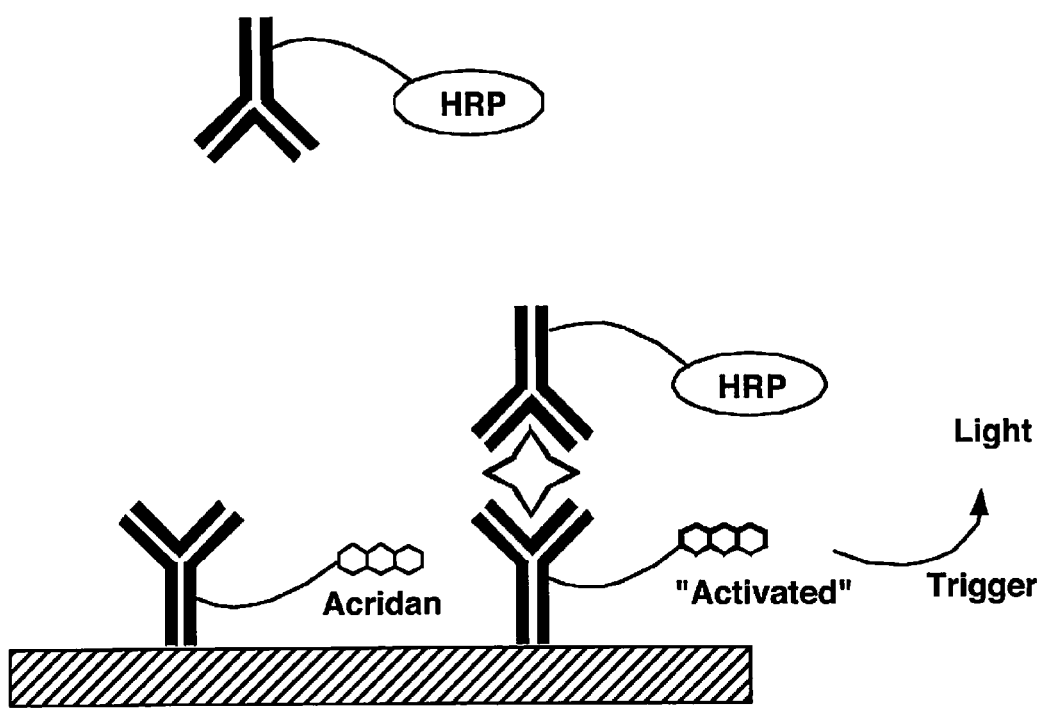
FIG. 1 is a schematic diagram of the detection step of an immunoassay conducted according to the invention using a labeled capture antibody. Addition of trigger solution results in chemiluminescence.

Alkyl—A branched, straight chain or cyclic hydrocarbon group containing from 1-20 carbons which can be substituted with 1 or more substituents other than H. Lower alkyl as used herein refers to those alkyl groups containing up to 8 carbons.

Analyte—A substance in a sample to be detected in an assay. One or more substances having a specific binding affinity to the analyte will be used to detect the analyte. The analyte can be a protein, a peptide, an antibody, or a hapten to which an antibody that binds it can be made. The analyte can be a nucleic acid or oligonucleotide which is bound by a complementary nucleic acid or oligonucleotide. The analyte can be any other substance which forms a member of a specific binding pair. Other exemplary types of analytes include drugs such as steroids, hormones, proteins, glycoproteins, mucoproteins, nucleoproteins, phosphoproteins, drugs of abuse, vitamins, antibacterials, antifungals, antivirals, purines, antineoplastic agents, amphetamines, azepine compounds, nucleotides, and prostaglandins, as well as metabolites of any of these drugs, pesticides and metabolites of pesticides, and receptors. Analyte also includes cells, viruses, bacteria and fungi.

Antibody—includes the full immunoglobulin as well as native and engineered fragments.

Aralkyl—An alkyl group substituted with an aryl group. Examples include benzyl, benzyhydryl, trityl, and phenylethyl.

Aryl—An aromatic ring-containing group containing 1 to 5 carbocyclic aromatic rings, which can be substituted with 1 or more substituents other than H.

Biological material—includes, for example. whole blood, anticoagulated whole blood, plasma, serum, tissue, animal and plant cells, cellular content, viruses, and fungi.

Chemiluminescent compound—A compound which undergoes a reaction resulting in it being converted into another compound formed in an electronically excited state. The excited state may be either a singlet or triplet excited state. The excited state may directly emit light upon relaxation to the ground state or may transfer excitation energy to an emissive energy acceptor, thereby returning to the ground state. The energy acceptor is raised to an excited state in the process and emits light.

Heteroalkyl—An alkyl group in which at least one of the ring or non-terminal chain carbon atoms is replaced with a heteroatom selected from N, O, or S.

Heteroaryl—An aryl group in which one to three of the ring carbon atoms is replaced with a heteroatom selected from N, O, or S. Exemplary groups include pyridyl, pyrrolyl, thienyl, furyl, quinolyl and acridnyl groups.

Magnetic particles—As used herein encompasses particulate material having a magnetically responsive component. Magnetically responsive includes ferromagnetic, paramagnetic and superparamagnetic materials. One exemplary magnetically responsive material is magnetite. Particles can have a solid core portion that is magnetically responsive and is surrounded by one or more non-magnetically responsive layers. Alternately the magnetically responsive portion can be a layer around or can be particles disposed within a non-magnetically responsive core.

Sample—A mixture containing or suspected of containing an analyte to be measured in an assay. Analytes include for example proteins, peptides, nucleic acids, hormones, antibodies, drugs, and steroids Typical samples which can be used in the methods of the invention include bodily fluids such as blood, which can be anticoagulated blood as is commonly found in collected blood specimens, plasma, serum, urine, semen, saliva, cell cultures, tissue extracts and the like. Other types of samples include solvents, seawater, industrial water samples, food samples and environmental samples such as soil or water, plant materials, eukaryotes, bacteria, plasmids, viruses, fungi, and cells originated from prokaryotes.

Solid support—a material having a surface upon which assay components are immobilized. Materials can be in the form of particles, microparticles, nanoparticles, metal colloids, fibers, sheets, beads, membranes, filters and other supports such as test tubes, microwells, chips, glass slides, and microarrays.

Specific binding pair member, specific binding partner—A molecule, including biological molecules, having a specific binding affinity for another substance including DNA, RNA, oligonucleotides, antibodies, antibody fragments, antibody-DNA chimeras, antigens, haptens, proteins, peptides, lectins, avidin, streptavidin and biotin. Specific binding partners can be conjugated to one or more molecules of either an activator or a chemiluminescent compound.

Substituted—Refers to the replacement of at least one hydrogen atom on a group by a non-hydrogen group. It should be noted that in references to substituted groups it is intended that multiple points of substitution can be present unless clearly indicated otherwise.

Test device—A vessel or apparatus for containing the sample and other components of an assay according to the present invention. Included are, for example, test tubes of various sizes and shapes, microwell plates, chips and slides on which arrays are formed or printed, test strips and membranes.

The present invention is concerned with rapid and simple assay methods for detecting the presence, location, or amount of substances by means of specific binding pair reactions. The methods require the use of an immobilized chemiluminescent compound, an activator compound conjugated to a specific binding partner for inducing a chemiluminescent reaction, and a trigger solution. The methods involve one or more specific binding pair reactions for detecting the analyte. As a result of a labeled specific binding partner binding to the analyte, an activator is brought into proximity to an immobilized chemiluminescent compound so that it is effective to activate a reaction generating chemiluminescence upon addition of a trigger solution. The activator-labeled specific binding partner is provided to the system in excess to the amount needed to bind all of the analyte. The excess unbound activator conjugate need not be removed prior to addition of trigger solution and detection since it does not participate in the reaction.

The present methods thus differ from conventional test methods in that the chemiluminescent compound and the activator are both constrained at a solid support in operable proximity to permit a chemiluminescent reaction to be performed upon addition of a trigger solution. The presence of excess non-immobilized activator, if not removed, does not defeat the ability to perform sensitive specific binding assays. This finding was not expected or predictable.

Significantly, it has been found that assay formats that reverse the means of immobilizing the chemiluminescent compound and activator do not permit assays to be performed successfully in a no wash format. When the activator is immobilized on the solid support and the chemiluminescent compound is provided as a conjugate with specific binding partner for direct or indirect binding to an analyte, followed by addition of trigger solution, the amount of light produced can not be correlated to the amount of analyte. Without being bound to any particular theory, it is believed that at least one factor contributing to the failure of these reversed formats is that excess chemiluminescent compound-specific binding partner conjugate not bound to the analyte is free to move about the assay solution or mixture and be in operable proximity to the immobilized activator.

In one embodiment there are provided assay methods, in particular binding assay methods, in which an immobilized chemiluminescent compound and an activator conjugate are brought into operable proximity via at least one specific binding reaction due to the presence of an analyte, wherein the bound activator conjugate activates a reaction generating chemiluminescence upon addition of a trigger solution for detecting the presence, location or amount of the analyte.

In one embodiment the present methods also differ from conventional test methods in not removing the unbound activator conjugate present in great excess to the amount specifically associated with the analyte. Samples containing analyte, activator conjugate, and trigger solution can be added sequentially to a test vessel, without washing or separations, and the luminescence read. Alternately, sample and activator conjugate can be pre-mixed and added to the test vessel containing a specific binding partner for capturing the analyte and containing the immobilized chemiluminescent label before introducing the trigger solution. No washing or separation of excess unbound activator conjugate is required. Another point of difference with conventional chemiluminescent assays known in the art rests in the fact that neither the chemiluminescent compound nor the activator (e.g. peroxidase) that participates in light production is free to diffuse in solution. Both are spatially constrained. Partially as a consequence of this, signal generation tends to be of short duration.

Conventional assays using chemiluminescent substrates and enzyme labeled conjugates provide the substrate in great excess to the amount of label enzyme. Frequently, the molar ratio of substrate/enzyme can exceed nine powers of ten, i.e., a billion-fold excess. It is believed to be necessary to supply such an enormous excess of chemiluminescent compound in order to ensure an adequate supply of substrate for continuous enzymatic turnover and that this process guarantees adequate detection sensitivity in assay methods. Applicants have found that it is possible to devise highly sensitive assay methods that reduce the ratio of chemiluminescent compound to activator by several orders of magnitude. In this regard these methods differ fundamentally from known methods.

Eliminating washing and separation steps as described above and as demonstrated in exemplary assays described below affords opportunities to simplify the design of assay protocols. The reduced number of operational steps decreases assay time, inter-assay variability from incomplete washing, and cost. At the same time it enhances the ability to automate and miniaturize assay performance with all of the inherent advantages attendant on automation and miniaturization.

Assays performed according to the present methods involve four steps. In a first step a solid support is provided in a test device for specifically capturing an analyte of interest. The solid support is provided with an immobilized specific binding partner for directly or indirectly binding an analyte to be detected. The solid support is further provided with chemiluminescent labeling compound immobilized thereon. The chemiluminescent label may be provided in a number of different ways as described in more detail below. In each variant the chemiluminescent label is stably or irreversibly attached to a substance or material in a way that renders it immobile. By "irreversibly" it is intended that the chemiluminescent label is not substantially removed from the solid support under the conditions of use in the intended assay. Passive or noncovalent attachment means are contemplated provided that the label is stably attached and retained on the solid support under the conditions of use. In a second step the analyte-containing sample and the activator conjugate are introduced to the test device having the solid support immobilized specific binding partner for the analyte and permitted to form specific binding complexes. The sample and activator conjugate can be added separately in either order, or simultaneously, or can be pre-mixed and added as a combination. An optional delay time to allow binding reactions to occur can be inserted at this point. Also an optional wash step can be included if desired to remove extraneous materials from the sample. In the third step a trigger solution is added to produce the chemiluminescence for detecting the analyte. Lastly the chemiluminescence is detected. Typically either peak light intensity level or total integrated light intensity is measured. The quantity of light can be related to the amount of the analyte by constructing a calibration curve according to generally known methods. When light emission ensues rapidly upon addition of trigger solution it is desirable to either mechanically time the onset of measurement to the addition by means of a suitable injector or to perform the addition with the test device already exposed to the detector. In this sense the third and fourth steps are essentially simultaneous. Optimum quanities of reactants, volumes, dilutions, incubation times for specific binding pair reactions, concentration of reactants, etc., can be readily determined by routine experimentation, by reference to standard treatises on methods of performing specific binding assays and using as a guide the specific examples described in detail below.

Assay Formats and Solid Supports

In the methods of the present invention, the chemiluminescent labeling compound is immobilized to a component of the test system. This can be accomplished in any of several ways. In embodiments of the present invention, the chemiluminescent label becomes immobilized to a surface of a solid support. A means is provided for attracting the analyte to the surface, e.g., by an unlabeled specific binding partner for the analyte. The chemiluminescent label becomes associated with the activator by virtue of a specific binding reaction bringing the activator near the immobilized chemiluminescent label attached to the solid support. Then the trigger solution is added and chemiluminescence measured.

Figure 2:
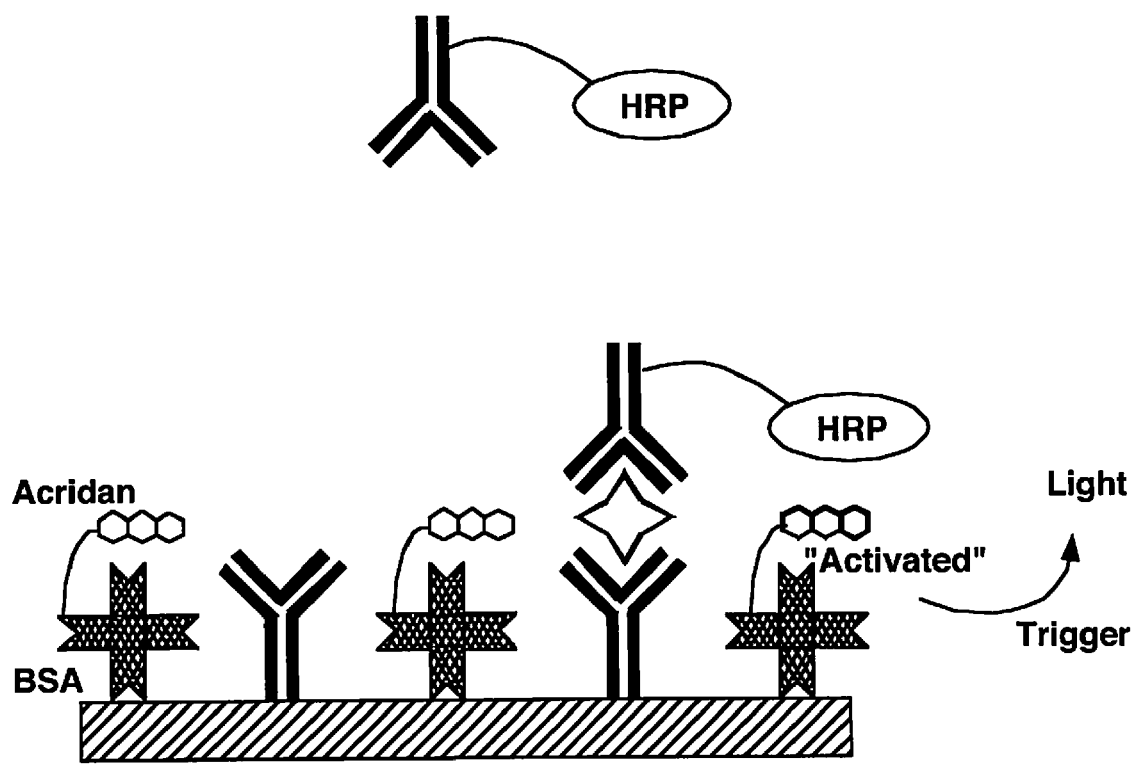
FIG. 2 is a schematic diagram of the detection step of another immunoassay conducted according to the invention using labeled blocking protein and an unlabeled capture antibody. Addition of trigger solution results in chemiluminescence.

In one embodiment the chemiluminescent label is covalently linked to an immobilized specific binding partner for the analyte. An example would be a labeled capture antibody or antibody fragment immobilized on the wells of a microplate or on a particle. Immobilization of the specific binding partner can be by covalent linkage or by an adsorption process. In this format, depicted in FIG. 1, the chemiluminescent label becomes associated with the activator by virtue of two specific binding partners both binding an analyte in a "sandwich" format. In another embodiment, depicted in FIG. 2, the chemiluminescent label is covalently linked to an auxiliary substance that is immobilized on the solid support in a random manner. Immobilization of the auxiliary substance can be by covalent linkage or by an adsorption process. The label is thereby distributed more or less uniformly about the surface of the solid support. A means is provided for attracting the analyte to the surface, e.g., by an unlabeled specific binding partner for the analyte. The chemiluminescent label becomes associated with the activator by virtue of a specific binding reaction bringing the activator near the chemiluminescent label attached to the auxiliary substance attached or passively coated onto the surface of the support. In another embodiment the chemiluminescent label is covalently linked to an immobilized universal antibody that has binding affinity for an analyte specific capture antibody. In another embodiment the auxiliary substance to which the chemiluminescent label is covalently linked is a protein or peptide. Exemplary proteins include albumin or streptavidin. The chemiluminescent compound can be provided for immobilization by using a biotin-chemiluminescent compound conjugate. Assay formats of this type can provide the specific binding partner for the analyte as a biotin conjugate, or by direct immobilization to the solid support or by indirect attachment through a universal capture component such as a species specific anti-immunoglobulin. In another embodiment the auxiliary substance to which the chemiluminescent label is covalently linked is a synthetic polymer. Assay formats using polymeric auxiliaries for immobilizing the chemiluminescent compound can provide the specific binding partner for the analyte as a biotin conjugate, or by direct immobilization to the solid support or by indirect attachment through a universal capture component such as a species specific immunoglobulin.

Figure 3:
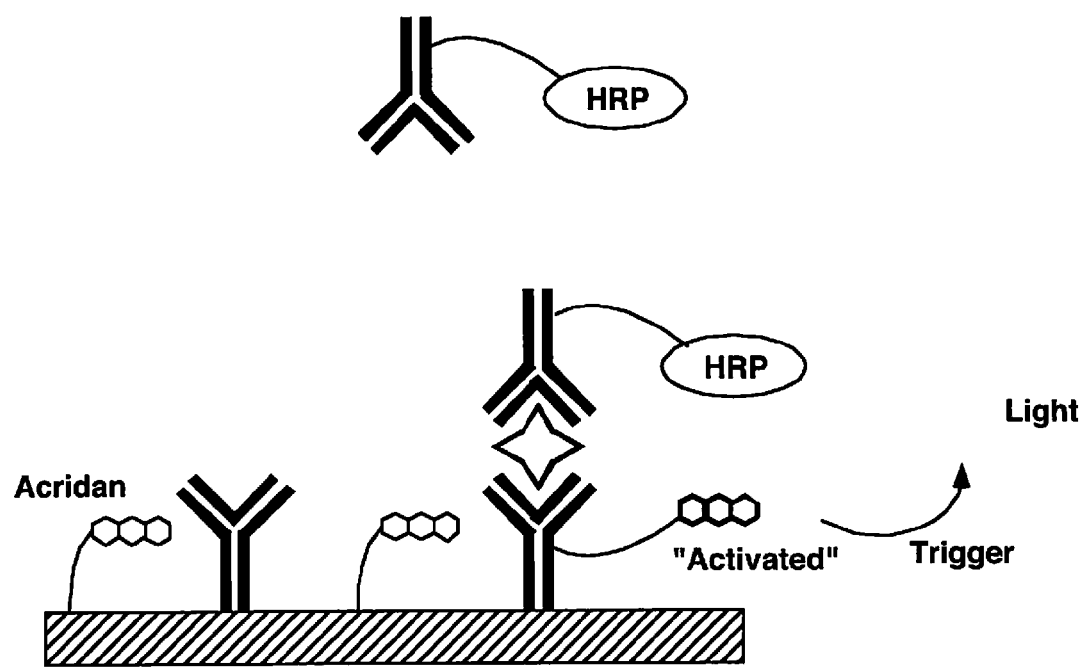
FIG. 3 is a schematic diagram of the detection step of another immunoassay conducted according to the invention using labeled solid surface and an unlabeled capture antibody. Addition of trigger solution results in chemiluminescence.

In another embodiment, the chemiluminescent label is covalently linked to the surface of the solid support. As depicted in FIG. 3, the label is thereby distributed more or less uniformly about the surface of the solid support. A means is provided for attracting the analyte to the surface, e.g., by an unlabeled specific binding partner for the analyte. The chemiluminescent label becomes associated with the activator by virtue of a specific binding reaction bringing the activator near the chemiluminescent label directly attached to the surface of the support. Then, without washing or separation, the trigger solution is added and chemiluminescence measured.

Figure 7:
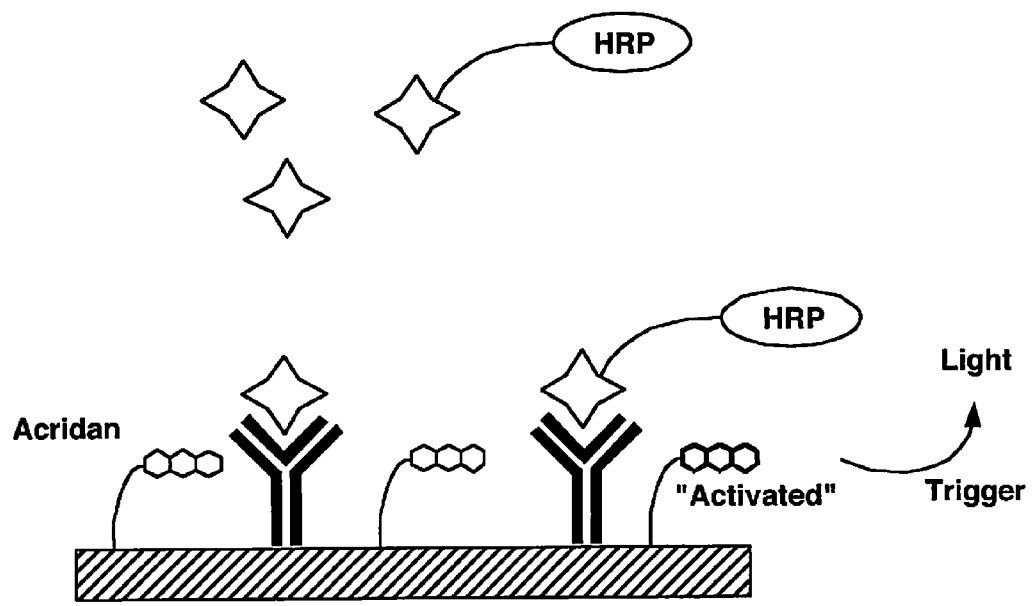
FIG. 7 is a schematic diagram of the detection step of a competitive immunoassay conducted according to the invention using a labeled solid phase, an immobilized capture antibody and a labeled analyte or analyte analog. Addition of trigger solution results in chemiluminescence.

In another embodiment an analog of the analyte is used comprising an activator-analyte analog conjugate. In another embodiment a labeled analyte is used comprising an activator-analyte conjugate. The activator-analyte analog conjugate or activator-analyte conjugate and analyte will competitively bind with the specific binding partner for the analyte. It will be apparent that in this type of assay method a negative correlation between the amount of analyte in the sample and the intensity of chemiluminescence will result. (FIG. 7)

Figure 6:
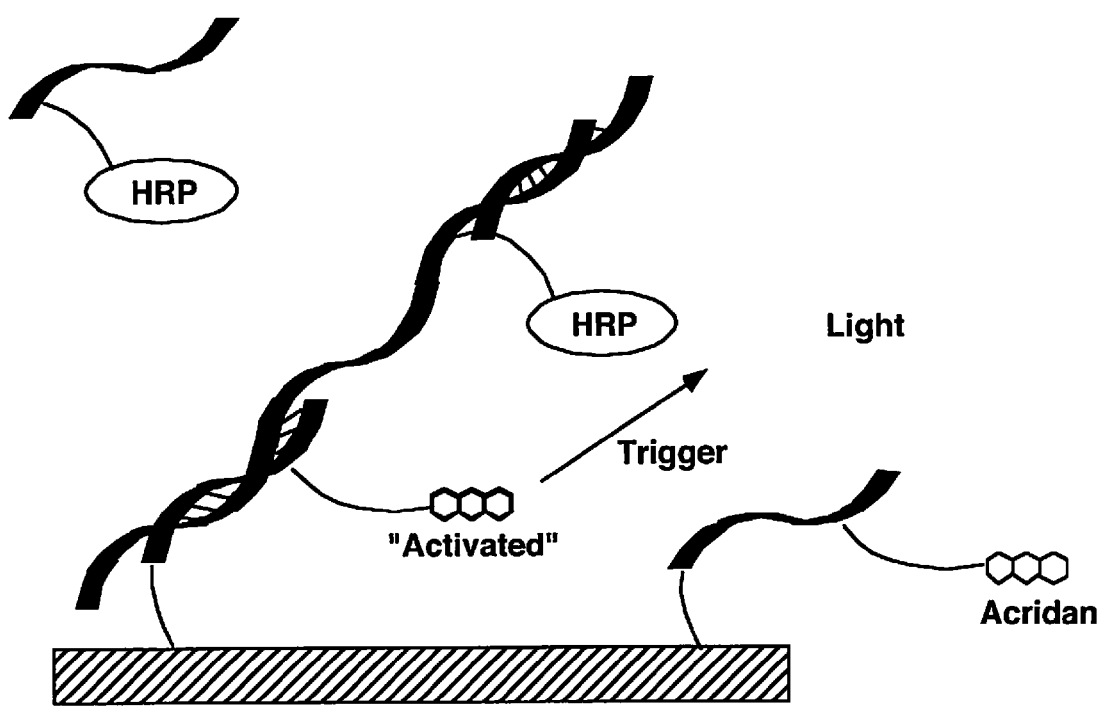
FIG. 6 is a schematic diagram of the detection step of a nucleic acid hybridization assay conducted according to the invention using a labeled capture nucleic acid. Addition of trigger solution results in chemiluminescence.

In addition to attachment of chemiluminescent label through antibodies for binding antigens or other proteins or other antibodies via an immunoassay, the present methods can use chemiluminescent-labeled nucleic acids for detecting nucleic acids through binding of complementary nucleic acids. The use in this regard is not particularly limited with regard to the size of the nucleic acid, the only criterion being that the complementary partners be of sufficient length to permit stable hybridization. Nucleic acids as used herein include gene length nucleic acids, shorter fragments of nucleic acids, polynucleotides and oligonucleotides, any of which can be single or double stranded. In the practice of the invention using nucleic acids as specific binding partners, a nucleic acid is covalently attached or physically immobilized on a surface of a solid support to capture an analyte nucleic acid. The chemiluminescent label can be attached to the capture nucleic acid, as shown schematically in FIG. 6, or the label can be associated with the support as explained above. The capture nucleic acid will have full or substantially full sequence complementarity to a sequence region of the analyte nucleic acid. When substantially complementary, the capture nucleic acid may possess a terminal overhanging portion, a terminal loop portion or an internal loop portion that is not complementary to the analyte provided that it does not interfere with or prevent hybridization with the analyte. The reverse situation may also occur where the overhang or loop resides within the analyte nucleic acid. Capture nucleic acid, analyte nucleic acid, a conjugate of an activator, and a third nucleic acid are allowed to hybridize. The third nucleic acid is substantially complementary to a sequence region of the analyte nucleic acid different from the region complementary to the capture nucleic acid. The hybridization of the capture nucleic acid and activator conjugate nucleic acid with the analyte can be performed consecutively in either order or simultaneously. As a result of this process, the chemiluminescent label becomes associated with the activator by virtue of specific hybridization reactions bringing the activator near the chemiluminescent label attached to the surface of the support. Trigger solution is provided and chemiluminescence detected as described above.

Another embodiment comprises a variation wherein a conjugate of the analyte with the activator is used. The analyte nucleic acid-activator conjugate and analyte nucleic acid will competitively bind with the specific binding partner for the analyte nucleic acid. It will be apparent that in this type of assay method a negative correlation between the amount of analyte in the sample and the intensity of chemiluminescence will result.

In addition to antibody-based and nucleic acid-based systems, other specific binding pairs as are generally known to one of ordinary skill in the art of binding assays can serve as the basis for test methods according to the present invention. Antibody-hapten pairs can also be used. Fluorescein/antifluorescein, digoxigenin/anti-digoxigenin, and nitrophenyl/anti-nitrophenyl pairs are exemplary. As a further example, the well known (strept)avidin/biotin binding pair can be utilized. To illustrate one way in which this binding pair could be used a streptavidin-chemiluminescent label conjugate can be covalently linked or adsorbed onto a solid support. A biotin-labeled analyte and an activator conjugate is then added, wherein the conjugate is attached to an anti-biotin antibody or anti-analyte antibody. After complexes are allowed to form the trigger solution is added and detection conducted as above. In another embodiment avidin or streptavidin is deposited on a solid support. A biotin-chemiluminescent compound conjugate is bound to avidin and a biotinylated antibody is also bound. In another embodiment biotin is linked to the solid support and used to capture avidin or streptavidin. A biotinylated antibody is also bound. The chemiluminescent compound can be affixed to the solid support either by binding a biotin-chemiluminescent compound conjugate to the (strept)avidin or by labeling the surface directly with the chemiluminescent compound. Additional specific binding partners known in the art include Fab portion of antibodies, lectin-carbohydrate, protein A-IgG, and hormone-hormone receptor. It is to be understood that indirect binding of chemiluminescent compound to the solid support can be employed in the service of the present invention. These and other examples that will occur to one of skill in the art are considered to be within the scope of the present inventive methods.

Solid supports useful in the practice of the present invention can be of various materials, porosity, shapes, and sizes. Materials already in use in binding assays including microwell plates of the 96-well, 384-well, or higher number varieties, test tubes, sample cups, plastic spheres, cellulose, paper or plastic test strips, latex particles, polymer particles having diameters of 0.10-50 µm, silica particles having diameters of 0.10-50 magnetic particles, especially those having average diameters of 0.1-10 µm, nanoparticles of various materials, and metal colloids can all provide a useful solid support for attachment of chemiluminescent labels and for immobilizing specific binding partners. Magnetic particles can comprise a magnetic metal, metal oxide or metal sulfide core, which is generally surrounded by an adsorptively or covalently bound layer to shield the magnetic component. The magnetic component can be iron, iron oxide or iron sulfide, wherein iron is $Fe^{2+}$ or $Fe^{3+}$ or both. Usable materials in this class include, e.g., magnetite, maghemite, and pyrite. Other magnetic metal oxides include $MnFe_2O_4$, $NiFe_2O_4$, and $CoFe_2O_4$. The magnetic component can, e.g., be a solid core that is surrounded by a nonmagnetic shell, or can be a core of interspersed magnetic and nonmagnetic material, or can be a layer surrounding a nonmagnetic core, optionally surrounded by another nonmagnetic shell. The nonmagnetic material in such magnetic particles can be silica, synthetic polymers such as polystyrene, Merrifield resin, polyacrylates or styrene-acrylate copolymers, or it can be a natural polymer such as agarose or dextran.

The present disclosure teaches methods of functionalizing such materials for use in the present assay methods. In particular, methods are disclosed for attaching both a chemiluminescent labeling compound and a specific binding partner, such as an antibody, to the same surface, especially to the wells of a microplate or a microparticle. Suitable supports used in assays include synthetic polymer supports, such as polystyrene, polypropylene, substituted polystyrene (e.g., aminated or carboxylated polystyrene), polyacrylamides, polyamides, polyvinylchloride, glass beads, silica particles, functionalized silica particles, metal colloids, agarose, nitrocellulose, nylon, polyvinylidenedifluoride, surface-modified nylon and the like.

Chemiluminescent Label Compounds

The compounds used as chemiluminescent labels in the practice of the present invention have the general formula CL-L-RG wherein CL denotes a chemiluminescent moiety, L denotes a linking moiety to link the chemiluminescent moiety and a reactive group, and RG denotes a reactive group moiety for coupling to another material. The terms 'chemiluminescent group' and 'chemiluminescent moiety' are used interchangeably as are the terms 'linking moiety' and 'linking group'. The chemiluminescent moiety CL comprises a compound which undergoes a reaction with an activator resulting in it being converted into an activated compound. Reaction of the activated compound with a trigger solution forms an electronically excited state compound. The excited state may be either a singlet or triplet excited state. The excited state may directly emit light upon relaxation to the ground state or may transfer excitation energy to an emissive energy acceptor, thereby returning to the ground state. The energy acceptor is raised to an excited state in the process and emits light. It is desirable but not necessary, that the chemiluminescent reaction of the CL group, the activator and the trigger solution be rapid, taking place over a very brief time span; in one embodiment reaching peak intensity within a few seconds.

In one embodiment of the invention the chemiluminescent compounds are capable of being oxidized to produce chemiluminescence in the presence of the activator and a trigger solution. An exemplary class of compounds which by incorporation of a linker and reactive group could serve as the chemiluminescent label include aromatic cyclic diacylhydrazides such as luminol and structurally related cyclic hydrazides including isoluminol, aminobutylethylisoluminol (ABEI), aminohexylethylisoluminol (AHEI), 7-dimethylaminonaphthalene-1,2-dicarboxylic acid hydrazide, ring-substituted aminophthalhydrazides, anthracene-2,3-dicarboxylic acid hydrazides, phenanthrene-1,2-dicarboxylic acid hydrazides, pyrenedicarboxylic acid hydrazides, 5-hydroxyphthal-hydrazide, 6-hydroxyphthalhydrazide, as well as other phthalazinedione analogs disclosed in U.S. Pat. No. 5,420,275 to Masuya et al. and in U.S. Pat. No. 5,324,835 to Yamaguchi.

It is considered that any compound known to produce chemiluminescence by the action of hydrogen peroxide and a peroxidase will function as the chemiluminescent moiety of the chemiluminescent label compound used in the present invention. Numerous such compounds of various structural classes, including xanthene dyes such as fluorescein, eosin, rhodamine dyes, or rhodol dyes, aromatic amines and heterocyclic amines are known in the art to produce chemiluminescence under these conditions. Another example is the compound MCLA, 2-methyl-6-(p-methoxyphenyl)-3,7-dihydroimidazo[1,2-a]pyrazin-3-one having the formula:

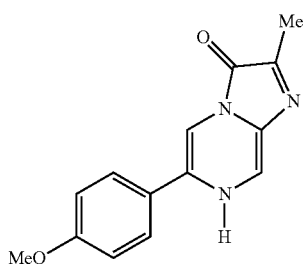

Another example is indole acetic acid, another is isobutyraldehyde, the latter typically being accompanied by a fluorescent energy acceptor for increasing the output of visible light. Trihydroxyaromatic compounds pyrogallol, phloroglucinol and purpurogallin, individually or in combination, are other examples of compounds that can serve as chemiluminescent moieties in the chemiluminescent labeling compounds of the invention.

In one embodiment a group of chemiluminescent label compounds comprising an acridan ketenedithioacetal useful in the methods of the invention comprises acridan compounds having formula I

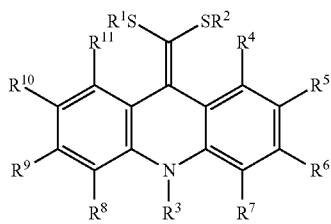

wherein at least one of the groups $R^1$-$R^{11}$ is a labeling substituent of the formula

-L-RG wherein L is a linking group which can be a bond or another divalent or polyvalent group, RG is a reactive group which enables the chemiluminescent labeling compound to be bound to another compound, $R^1$, $R^2$ and $R^3$ are organic groups containing from 1 to 50 non-hydrogen atoms, and each of $R^4$-$R^{11}$ is hydrogen or a noninterfering substituent. The labeling substituent -L-RG can be present on one of $R^1$ or $R^2$ although it can also be present as a substituent on $R^3$ or one of $R^4$-$R^{11}$.

The groups $R^1$ and $R^2$ in the compound of formula I can be any organic group containing from 1 to about 50 non hydrogen atoms selected from C, N, O, S, P, Si and halogen atoms which allows light production. By the latter is meant that when a compound of formula I undergoes a reaction of the present invention, an excited state product compound is produced and can involve the production of one or more chemiluminescent intermediates. The excited state product can emit the light directly or can transfer the excitation energy to a fluorescent acceptor through energy transfer causing light to be emitted from the fluorescent acceptor. In one embodiment $R^1$ and $R^2$ are selected from substituted or unsubstituted alkyl, substituted or unsubstituted alkenyl, substituted or unsubstituted alkynyl, substituted or unsubstituted aryl, and substituted or unsubstituted aralkyl groups of 1-20 carbon atoms. When $R^1$ or $R^2$ is a substituted group, it can be substituted with 1-3 groups selected from carbonyl groups, carboxyl groups, tri($C_1$-$C_8$ alkyl)silyl groups, a $SO_3^-$ group, a $OSO_3^{-2}$ group, glycosyl groups, a $PO_3^-$ group, a $OPO_3^{-2}$ group, halogen atoms, a hydroxyl group, a thiol group, amino groups, quaternary ammonium groups, and quaternary phosphonium groups. In one embodiment, $R^1$ or $R^2$ is substituted with the labeling substituent of the formula -L-RG where L is a linking group and RG is a reactive group.

The group $R^3$ is an organic group containing from 1 to 50 non-hydrogen atoms selected from C, N, O, S, P, Si and halogen in addition to the necessary number of H atoms required to satisfy the valences of the atoms in the group. In one embodiment $R^3$ contains from 1 to 20 non-hydrogen atoms. In another embodiment the organic group is selected from the group consisting of alkyl, substituted alkyl, substituted or unsubstituted alkenyl, substituted or unsubstituted alkynyl, substituted or unsubstituted aryl, and substituted or unsubstituted aralkyl groups of 1-20 carbon atoms. In another embodiment groups for $R^3$ include substituted or unsubstituted $C_1$-$C_4$ alkyl groups, phenyl, substituted or unsubstituted benzyl groups, alkoxyalkyl, carboxyalkyl and alkylsulfonic acid groups. The group $R^3$ can be joined to either $R^7$ or $R^8$ to complete a 5 or 6-membered ring. In one embodiment, $R^3$ is substituted with the labeling substituent of the formula -L-RG.

In the compounds of formula I, the groups $R^4$-$R^{11}$ each are independently H or a substituent group which permits the excited state product to be produced and generally contain from 1 to 50 atoms selected from C, N, O, S, P, Si and halogens. Representative substituent groups which can be present include, without limitation, alkyl, substituted alkyl, aryl, substituted aryl, aralkyl, alkenyl, alkynyl, alkoxy, aryloxy, halogen, amino, substituted amino, carboxyl, carboalkoxy, carboxamide, cyano, and sulfonate groups. Pairs of adjacent groups, e.g., $R^4$-$R^5$ or $R^5$-$R^6$, can be joined together to form a carbocyclic or heterocyclic ring system comprising at least one 5 or 6-membered ring which is fused to the ring to which the two groups are attached. Such fused heterocyclic rings can contain N, O or S atoms and can contain ring substituents other than H such as those mentioned above. One or more of the groups $R^4$-$R^{11}$ can be a labeling substituent of the formula -L-RG. In one embodiment $R^4$-$R^{11}$ are selected from hydrogen, halogen and alkoxy groups such as methoxy, ethoxy, t-butoxy and the like. In another embodiment a group of compounds has one of $R^5$, $R^6$, $R^9$ or $R^{10}$ as a halogen and the other of $R^4$-$R^{11}$ are hydrogen atoms.

Substituent groups can be incorporated in various quantities and at selected ring or chain positions in the acridan ring in order to modify the properties of the compound or to provide for convenience of synthesis. Such properties include, e.g., chemiluminescence quantum yield, rate of reaction with the enzyme, maximum light intensity, duration of light emission, wavelength of light emission and solubility in the reaction medium. Specific substituents and their effects are illustrated in the specific examples below, which, however, are not to be considered limiting the scope of the invention in any way. For synthetic expediency compounds of formula I desirably have each of $R^4$ to $R^{11}$ as a hydrogen atom.

In another embodiment a group of compounds have formula II wherein each of $R^4$ to $R^{11}$ are hydrogen. The groups $R^1$, $R^2$ and $R^3$ are as defined above.

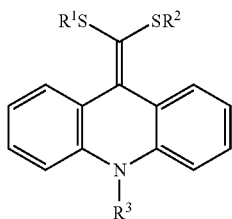

II

Labeling compounds of formulas I or II have the groups -L-RG as a substituent on the group $R^1$ or $R^2$. In an embodiment a labeling compound has formula III.

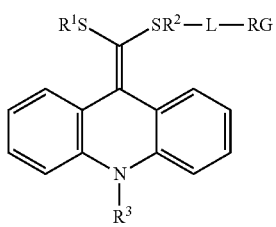

III

Representative labeling compounds and their use in attachment to other molecules and solid surfaces is described in the specific examples below.

Another class of chemiluminescent moieties include acridan esters, thioesters and sulfonamides disclosed in U.S. Pat. Nos. 5,491,072; 5,523,212; 5,593,845; and 6,030,803. Chemiluminescent labeling compounds in this class have a chemiluminescent moiety CL of formula IV below wherein Z is O, S or $NR^{11}SO_2Ar$, wherein $R^{11}$ is alkyl or aryl, wherein Ar is aryl or alkyl-substituted aryl, wherein $R^1$ is $C_{1-8}$ alkyl, halo-substituted $C_{1-8}$ alkyl, aralkyl, aryl, or aryl substituted with alkyl, alkenyl, alkynyl, aralkyl, aryl, alkoxy, alkoxyalkyl, halogen, carbonyl, carboxyl, carboxamide, cyano, trifluoromethyl, trialkylammonium, nitro, hydroxy, amino and mercapto groups, wherein $R^2$ is selected from alkyl, heteroalkyl, aryl, and aralkyl groups, and wherein $R^{3-10}$ are each hydrogen or 1 or 2 substituents are selected from alkyl, alkoxy, hydroxy, and halogen, and the remaining of $R^{3-10}$ are hydrogen. In one embodiment each of $R^{3-10}$ is hydrogen and $R^1$ is a labeling substituent. In another embodiment one of $R^{3-10}$ is a labeling substituent and the others of $R^{3-10}$ are hydrogen.

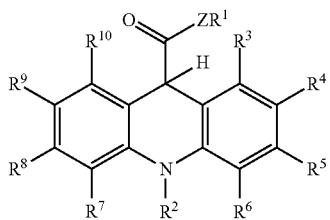

IV

Another class of chemiluminescent moieties includes the heterocyclic compounds disclosed in U.S. Pat. Nos. 5,922,558; 6,696,569; and 6,891,057. In one embodiment the compounds comprise a heterocyclic ring, comprising a nitrogen, oxygen or sulfur-containing five or six-membered ring or multiple ring group to which is bonded an exocyclic double bond, the terminal carbon of which is substituted with two atoms selected from oxygen, and sulfur atoms.

In another embodiment the chemiluminescent labeling compounds have a chemiluminescent acridan moiety CL of formula V below wherein $R^1$ is selected from alkyl, alkenyl, alkynyl, aryl, and aralkyl groups of 1-20 carbon atoms any of which can be substituted with 1-3 groups selected from carbonyl groups, carboxyl groups, $tri(C_1-C_8$ alkyl)silyl groups, a $SO_3^-$ group, a $OSO_3^{-2}$ group, glycosyl groups, a $PO_3^-$ group, a $OPO_3^{-2}$ group, halogen atoms, a hydroxyl group, a thiol group, amino groups, quaternary ammonium groups, or quaternary phosphonium groups, wherein X is selected from $C_1-C_8$ alkyl, aryl, aralkyl groups, alkyl or aryl carboxyl groups having from 1-20 carbon atoms, $tri(C_1-C_8$ alkyl)silyl groups, a $SO_3^-$ group, glycosyl groups and phosphoryl groups of the formula PO(OR')(OR") wherein R' and R" are independently selected from $C_1-C_8$ alkyl, cyanoalkyl, aryl and aralkyl groups, trialkylsilyl groups, alkali metal cations, alkaline earth cations, ammonium and trialkylphosphonium cations, wherein $Z^1$ is selected from O and S atoms, wherein $R^6$ is selected from substituted or unsubstituted $C_1-C_4$ alkyl, phenyl, benzyl, alkoxyalkyl and carboxyalkyl groups, wherein $R^{7-14}$ are each hydrogen or 1 or 2 substituents are selected from alkyl, alkoxy, hydroxy, and halogen and the remaining of $R^{7-14}$ are hydrogen. In one embodiment each of $R^{7-14}$ is hydrogen and $R^1$ is a labeling substituent. In another embodiment one of $R^{7-14}$ is a labeling substituent and the others of $R^{7-14}$ are hydrogen.

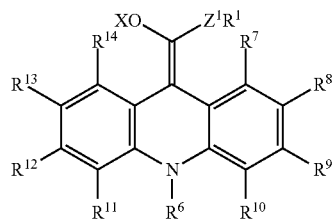

V

In another embodiment the chemiluminescent labeling compounds have a chemiluminescent moiety CL of formula VI below wherein $R^1$ is selected from alkyl, alkenyl, alkynyl, aryl, and aralkyl groups of 1-20 carbon atoms any of which can be substituted with 1-3 groups selected from carbonyl groups, carboxyl groups, $tri(C_1-C_8$ alkyl)silyl groups, a $SO_3^-$ group, a $OSO_3^{-2}$ group, glycosyl groups, a $PO_3^-$ group, a $OPO_3^{-2}$ group, halogen atoms, a hydroxyl group, a thiol group, amino groups, quaternary ammonium groups, or quaternary phosphonium groups, wherein X is selected from $C_1-C_8$ alkyl, aryl, aralkyl groups, alkyl or aryl carboxyl groups having from 1-20 carbon atoms, $tri(C_1-C_8$ alkyl)silyl groups, a $SO_3^-$ group, glycosyl groups and phosphoryl groups of the formula PO(OR')(OR") wherein R' and R" are independently selected from $C_1-C_8$ alkyl, cyanoalkyl, aryl and aralkyl groups, trialkylsilyl groups, alkali metal cations, alkaline earth cations, ammonium and trialkylphosphonium cations, wherein $Z^1$ and $Z^2$ are each selected from O and S atoms and wherein $R^2$ and $R^3$ are independently selected from hydrogen and $C_1-C_8$alkyl.

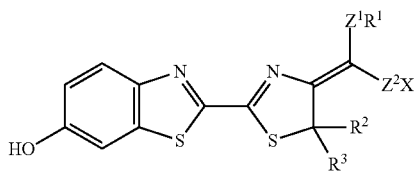

VI

Linking group (L). The linking group in any of the chemiluminescent compounds used in the present invention can be a bond, an atom, divalent groups and polyvalent groups, or a straight, or branched chain of atoms some of which can be part of a ring structure. The substituent usually contains from 1 to about 50 non-hydrogen atoms, more usually from 1 to about 30 non-hydrogen atoms. In another embodiment atoms comprising the chain are selected from C, O, N, S, P, Si, B, and Se atoms. In another embodiment atoms comprising the chain are selected from C, O, N, P and S atoms. The number of atoms other than carbon in the chain is normally from 0-10. Halogen atoms can be present as substituents on the chain or ring. Typical functional groups comprising the linking substituent include alkylene, arylene, alkenylene, ether, peroxide, carbonyl as a ketone, ester, carbonate ester, thioester, or amide group, amine, amidine, carbamate, urea, imine, imide, imidate, carbodiimide, hydrazino, diazo, phosphodiester, phosphotriester, phosphonate ester, thioether, disulfide, sulfoxide, sulfone, sulfonate ester, sulfate ester, and thiourea groups. In another embodiment the group is an alkylene chain of 1-20 atoms terminating in a —C$_2$—, —O—, —S—, —NH—, —NR—, —SiO—, —C(=O)—, —OC(=O)—, —C(=O)O—, —SC(=O)—, —C(=O)S—, —NRC(=O)—, —NRC(=S)—, or —C(=O)NR— group, wherein R is C$_{1-8}$ alkyl. In another embodiment the linking group is a poly(alkylene-oxy) chain of 3-30 atoms terminating in a —CH$_2$—, —O—, —S—, —NH—, —NR—, —SiO—, —C(=O)—, —OC(=O)—, —C(=O)O—, —SC(=O)—, —C(=O)S—, —NRC(=O)—, —NRC(=S)—, or —C(=O)NR— group, wherein R is C$_{1-8}$ alkyl.

Reactive group. The reactive group RG is an atom or group whose presence facilitates bonding to another molecule by covalent attachment or physical forces. In some embodiments, attachment of a chemiluminescent labeling compound of the present invention to another compound will involve loss of one or more atoms from the reactive group for example when the reactive group is a leaving group such as a halogen atom or a tosylate group and the chemiluminescent labeling compound is covalently attached to another compound by a nucleophilic displacement reaction. In other embodiments, attachment of a chemiluminescent labeling compound to another compound by covalent bond formation will involve reorganization of bonds within the reactive group as occurs in an addition reaction such as a Michael addition or when the reactive group is an isocyanate or isothiocyanate group. In still other embodiments, attachment will not involve covalent bond formation, but rather physical forces in which case the reactive group remains unaltered. By physical forces is meant attractive forces such as hydrogen bonding, electrostatic or ionic attraction, hydrophobic attraction such as base stacking, and specific affinity interactions such as biotin-streptavidin, antigen-antibody and nucleotide-nucleotide interactions.

TABLE 1

Reactive Groups for Chemical Binding of Labels to Organic and Biological Molecules a.) Amine reactive groups.

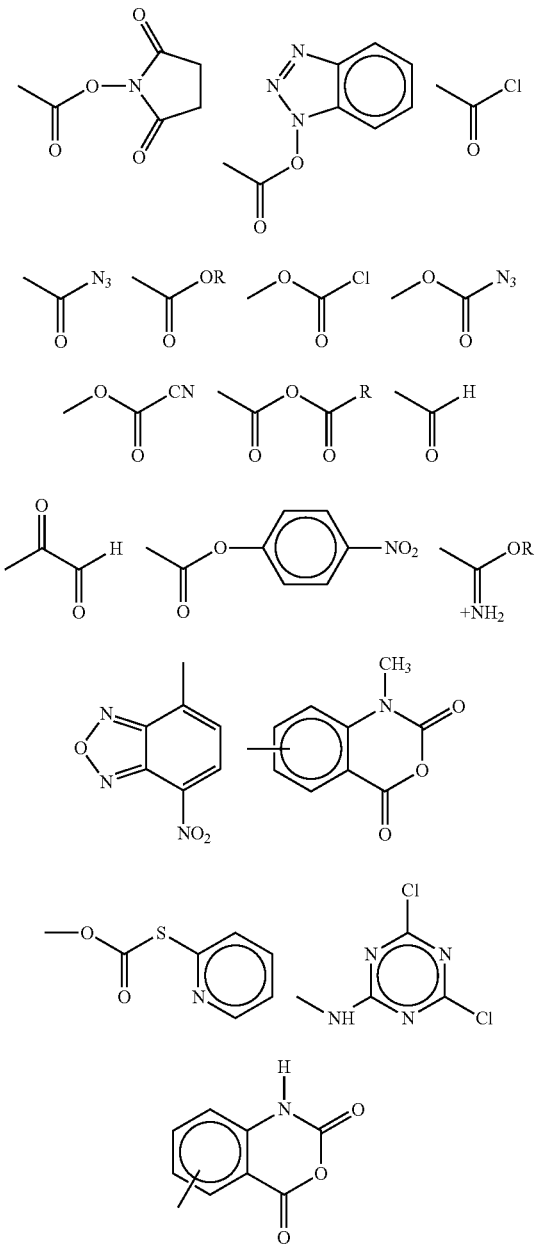

b.) Thiol reactive groups.

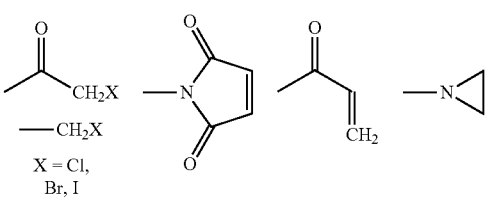

TABLE 1-continued

Reactive Groups for Chemical Binding of Labels to Organic and Biological Molecules

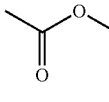

3) Carboxylic acid reactive groups.

—NH$_2$   —OH   —SH   —NHNH$_2$   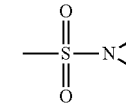

4) Hydroxyl reactive groups.

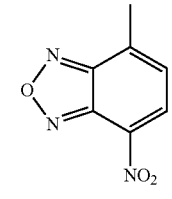

—N═C═S   —SO$_2$Cl   —N═C═O   —SO$_2$CH$_2$CF$_3$

5) Aldehyde/ketone reactive groups.

—NH$_2$   —ONH$_2$   —NHNH$_2$

6) Other reactive groups.

R—N$_3$   R—C≡CH   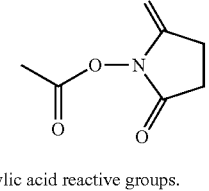

In one embodiment reactive groups include OH, NH$_2$, ONH$_2$, NHNH$_2$, COOH, SO$_2$CH$_2$CF$_3$, N-hydroxysuccinimide ester, N-hydroxysuccinimide ether and maleimide groups.

Bifunctional coupling reagents can also be used to couple labels to organic and biological molecules with moderately reactive groups (see L. J. Kricka, *Ligand-Binder Assays*, Marcel Dekker, Inc., New York, 1985, pp. 18-20, Table 2.2 and T. H Ji, "Bifunctional Reagents," *Methods in Enzymology*, 91, 580-609 (1983)). There are two types of bifunctional reagents: those that become incorporated into the final structure, and those that do not and serve only to couple the two reactants.

Activator Conjugate

The activator compound forms part of an activator-specific binding partner conjugate. The conjugate serves a dual function: 1) undergoing a specific binding reaction in proportion to the amount of the analyte in the assay through the specific binding partner portion, either directly or through an intermediary specific binding partner, and 2) activating the chemiluminescent compound through the activator portion. The activator portion of the conjugate is a compound that effects the activation of the chemiluminescent compound so that, in the presence of the trigger solution, chemiluminescence is produced. Compounds capable of serving as the activator include compounds with peroxidase-like activity including transition metal salts and'complexes and enzymes, especially transition metal-containing enzymes, most especially peroxidase enzymes. Transition metals useful in activator compounds include those of groups 3-12 of the periodic table, especially iron, copper, cobalt, zinc, manganese, and chromium. It should be noted that the activator molecules responsible for signal generation may operate within a physically confined radius and only have contact with a finite supply of chemiluminescent compound. This would seem to preclude large catalytic turnover in cases where the activator possesses that potential.

The peroxidase enzymes which can undergo the chemiluminescent reaction include e.g., lactoperoxidase, microperoxidase, myeloperoxidase, haloperoxidase, vanadium bromoperoxidase, horseradish peroxidase, fungal peroxidases, lignin peroxidase, peroxidase from Arthromyces ramosus, Mn-dependent peroxidase produced in white rot fungi, and soybean peroxidase. Other peroxidase mimetic compounds are known which are not enzymes but possess peroxidase-like activity including iron complexes, such as heme, and Mn-TPPS$_4$ (Y.-X. Ci, et al., Mikrochem. J., 52, 257-62 (1995)). These catalyze the chemiluminescent oxidation of substrates and are explicitly considered to be within the scope of the meaning of peroxidase as used herein.

Conjugates or complexes of a peroxidase and a biological molecule can also be used in the method for producing chemiluminescence, the only proviso being that the conjugate display peroxidase or peroxidase-like activity. Biological molecules which can be conjugated to one or more molecules of a peroxidase include DNA, RNA, oligonucleotides, antibodies, antibody fragments, antibody-DNA chimeras, antigens, haptens, proteins, peptides, lectins, avidin, streptavidin and biotin. Complexes including or incorporating a peroxidase, such as liposomes, micelles, vesicles and polymers which are functionalized for attachment to biological molecules, can also be used in the methods of the present invention.

Compositions of Matter

In another embodiment of the present invention there are provided assay materials comprising a solid support having immobilized thereon a chemiluminescent compound. In one embodiment the chemiluminescent compound is selected from any of the group of chemiluminescent compounds described above. In another embodiment the chemiluminescent compound is a substrate for a peroxidase enzyme. The quantity of the chemiluminescent compound immobilized on the solid support can vary over a range of loading densities. As an example, when the solid support is a particulate material, a loading in the range of 100-0.01 μg of chemiluminescent compound per mg of particle can be used. In another example a loading in the range of 5-0.1 μg of chemiluminescent compound per mg of particle can be used. The chemiluminescent compound is generally distributed randomly or uniformly onto the solid support. It may be immobilized on the surface or within accessible pores of the solid support. The chemiluminescent compound can be immobilized onto the solid support by covalent attachment. In this embodiment a chemiluminescent labeling compound having a reactive group is reacted with a functional group present on the solid support in order to form a covalent bond between the chemiluminescent compound and the solid support. In an alternative embodiment the chemiluminescent compound can be immobilized onto the solid support by means of one or more intermediary substances. In one example biotin is covalently attached to the solid support, the covalently attached biotin is bound to streptavidin and a biotin-chemiluminescent compound conjugate is then bound. In another example, streptavidin is adsorbed onto the solid support and a biotin-chemiluminescent compound conjugate is then bound. In another example a chemiluminescent compound conjugated to an auxiliary protein such as albumin is adsorbed or covalently linked onto the solid support. In another example a chemiluminescent compound conjugated to an antibody is adsorbed or covalently linked onto the solid support.

The solid support can be of various materials, porosity, shapes, and sizes such as microwell plates having 96-well, 384-well, or higher numbers of wells, test tubes, sample cups, plastic spheres, cellulose, paper or plastic test strips, latex particles, polymer particles having diameters of 0.10-50 µm, silica particles having diameters of 0.10-50 µm, magnetic particles, especially those having average diameters of 0.1-10 µm, and nanoparticles. In one embodiment the solid support comprises polymeric or silica particles having diameters of 0.10-50 µM, and can be magnetic particles as defined above.

The immobilized chemiluminescent compound of the present invention comprises a chemiluminescent label affixed to the solid support wherein the chemiluminescent label is provided by a chemiluminescent labeling compound having the general formula CL-L-RG wherein CL denotes a chemiluminescent moiety, L denotes a linking moiety to link the chemiluminescent moiety to a reactive group, and RG denotes a reactive group moiety for coupling to another material. The chemiluminescent moiety CL comprises a compound which undergoes a reaction with an activator resulting in it being converted into an activated compound. Reaction of the activated compound with a trigger solution forms an electronically excited state compound. The chemiluminescent moiety includes each class of compound described above under the heading "Chemiluminescent Label Compounds" including, without limitation, luminol, and structurally related cyclic hydrazides, acridan esters, thioesters and sulfonamides, and acridan ketenedithioacetal compounds.

In another embodiment of the present invention there are provided assay materials comprising a solid support having immobilized thereon a chemiluminescent compound and at least one specific binding substance having specific binding affinity for an analyte or having specific binding affinity for another substance having specific binding affinity for an analyte. In these embodiments the immobilized chemiluminescent compound is as described immediately above for embodiments comprising a solid support having a chemiluminescent compound immobilized thereon. The immobilized specific binding substances directly or indirectly bind an analyte through one or more specific affinity binding reactions. The specific binding substances include, without limitation, antibodies and antibody fragments, antigens, haptens and their cognate antibodies, biotin and avidin or streptavidin, protein A and IgG, complementary nucleic acids or oligonucleotides, lectins and carbohydrates.

Another embodiment of the present invention comprises a signaling system formed in an assay comprising a solid support having immobilized thereon 1) a chemiluminescent compound, 2) at least one specific binding substance having specific binding affinity for an analyte or having specific binding affinity for another substance having specific binding affinity for an analyte, 3) an analyte, and 4) an activator conjugate. The meaning of the terms 'solid support', 'chemiluminescent compound' and 'specific binding substance' and embodiments encompassed by these terms are identical to the meanings and embodiments established above for the assay materials considered as compositions of the present invention. Analytes that can form an element of the present signaling systems include any of the analytes identified above, the presence, location or amount of which is to be determined in an assay. The activator conjugate comprises an activator compound joined to an analyte-specific binding partner conjugate. The conjugate serves a dual function: 1) binding specifically to the analyte in the assay through the specific binding partner portion, either directly or through an intermediary specific binding partner, and 2) activating the chemiluminescent compound through the activator portion. The activator compound portion of the conjugate is a compound that effects the activation of the chemiluminescent compound so that, in the presence of the trigger solution, chemiluminescence is produced. Compounds capable of serving as the activator include compounds with peroxidase-like activity including transition metal salts and complexes and enzymes, especially transition metal-containing enzymes, especially peroxidase enzymes. Transition metals useful in activator compounds include those of groups 3-12 of the periodic table, especially iron, copper, cobalt, zinc, manganese, and chromium. The peroxidase which can undergo the chemiluminescent reaction include e.g., lactoperoxidase, microperoxidase, myeloperoxidase, haloperoxidase, vanadium bromoperoxidase, horseradish peroxidase, fungal peroxidases, lignin peroxidase, peroxidase from Arthromyces ramosus, Mn-dependent peroxidase produced in white rot fungi, and soybean peroxidase. Other compounds that possess peroxidase-like activity include iron complexes, such as heme, and Mn-TPPS$_4$.

Trigger Solution

The trigger solution provides a reactant necessary for generating the excited state compound necessary for chemiluminescence. The reactant may be one necessary for performing the chemiluminescent reaction by reacting directly with the chemiluminescent label. It may serve instead of or in addition to this function to facilitate the action of the activator compound. This will be the case, for example, when the activator is a peroxidase enzyme. In one embodiment the trigger solution comprises a peroxide compound. The peroxide component is any peroxide or alkyl hydroperoxide capable of reacting with the peroxidase. Exemplary peroxides include hydrogen peroxide, urea peroxide, and perborate salts. The concentration of peroxide used in the trigger solution can be varied within a range of values, typically from about $10^{-8}$ M to about 3 M, more commonly from about $10^{-3}$ M to about $10^{-1}$ M. A representative embodiment uses a peroxidase conjugate as the activator, an acridan labeled specific binding partner of an analyte wherein the acridan label is provided by reacting the specific binding partner with a compound of formula III above, and a trigger solution comprising hydrogen peroxide. The peroxide reacts with the peroxidase, presumably to change the oxidation state of the iron in the active site of the enzyme to a different oxidation state. This altered state of the enzyme reacts with the acridan label maintained in proximity to the enzyme. The chemiluminescent reaction comprises a further reaction of an intermediate formed from the chemiluminescent compound with peroxide to produce the ultimate reaction product and light.

Incorporation of certain enhancer compounds into the trigger solution promotes the reactivity of the enzyme or reduces background signal or performs both functions. Included among these enhancers are phenolic compounds and aromatic amines known to enhance other peroxidase reactions as described in U.S. Pat. Nos. 5,171,668 and 5,206,149, which are incorporated herein by reference. Substituted and unsubstituted arylboronic acid compounds and their ester and anhydride derivatives as disclosed in U.S. Pat. No. 5,512,451 and incorporated herein by reference are also considered to be within the scope of enhancers useful in the present invention. Exemplary enhancers include but are not limited to: p-phenylphenol, p-iodophenol, p-bromophenol, p-hydroxycinnamic acid, p-imidazolylphenol, acetaminophen, 2,4-dichlorophenol, 2-naphthol and 6-bromo-2-naphthol. Mixtures of more than one enhancer from those classes mentioned above can also be employed.

Additional enhancers found to be effective in enhancing the production of chemiluminescence from compounds of the present invention are derivatives of phenoxazine and phenothiazine having the formulas below.

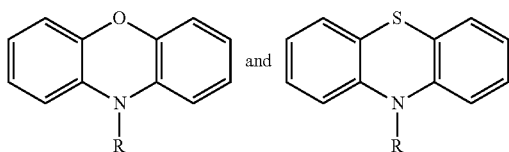

R groups substituted on the nitrogen atom of phenoxazine and phenothiazine enhancers include alkyl of 1-8 carbon atoms, and alkyl of 1-8 carbon atoms substituted with a sulfonate salt or carboxylate salt group. Exemplary enhancers include 3-(N-phenothiazinyl)-propanesulfonic acid salts, 3-(N-phenoxazinyl)propanesulfonic acid salts, 4-(N-phenoxazinyl)butanesulfonic acid salts, 5-(N-phenoxazinyl)-pentanoic acid salts and N-methylphenoxazine and related homologs. The concentration of enhancers used in the trigger solution can be varied within a range of values, typically from about $10^{-5}$ M to about $10^{-1}$ M, more commonly from about $10^{-4}$ M to about $10^{-2}$ M.

The detection reaction of the present invention is performed with a trigger solution which is typically in an aqueous buffer. Suitable buffers include any of the commonly used buffers capable of maintaining an environment permitting the chemiluminescent reaction to proceed. Typically the trigger solution will have a pH in the range of about 5 to about 10.5. Exemplary buffers include phosphate, borate, acetate, carbonate, tris(hydroxy-methylamino)methane [tris], glycine, tricine, 2-amino-2-methyl-1-propanol, diethanolamine MOPS, HEPES, MES and the like.

The trigger solution can also contain one or more detergents or polymeric surfactants to enhance the luminescence efficiency of the light-producing reaction or improve the signal/noise ratio of the assay. Nonionic surfactants useful in the practice of the present invention include by way of example polyoxyethylenated alkylphenols, polyoxyethylenated alcohols, polyoxyethylenated ethers and polyoxyethylenated sorbitol esters. Monomeric cationic surfactants, including quaternary ammonium salt compounds such as CTAB and quaternary phosphonium salt compounds can be used. Polymeric cationic surfactants including those comprising quaternary ammonium and phosphonium salt groups can also be used for this purpose.

In one embodiment the trigger solution is a composition comprising an aqueous buffer, a peroxide at a concentration of about $10^{-5}$ M to about 1 M, and an enhancer at a concentration of about $10^{-5}$ M to about $10^{-1}$ M. The composition may optionally contain additives including surfactants, metal chelating agents, and preservatives to prevent or minimize microbial contamination.

Detection

Light emitted by the present method can be detected by any suitable known means such as a luminometer, x-ray film, high speed photographic film, a CCD camera, a scintillation counter, a chemical actinometer or visually. Each detection means has a different spectral sensitivity. The human eye is optimally sensitive to green light, CCD cameras display maximum sensitivity to red light, X-ray films with maximum response to either UV to blue light or green light are available. Choice of the detection device will be governed by the application and considerations of cost, convenience, and whether creation of a permanent record is required. In those embodiments where the time course of light emission is rapid, it is advantageous to perform the triggering reaction to produce the chemiluminescence in the presence of the detection device. As an example the detection reaction may be performed in a test tube or microwell plate housed in a luminometer or placed in front of a CCD camera in a housing adapted to receive test tubes or microwell plates.

Uses

The present assay methods find applicability in many types of specific binding pair assays. Foremost among these are chemiluminescent enzyme linked immunoassays, such as an ELISA. Various assay formats and the protocols for performing the immunochemical steps are well known in the art and include both competitive assays and sandwich assays. Types of substances that can be assayed by immunoassay according to the present invention include proteins, peptides, antibodies, haptens, drugs, steroids and other substances that are generally known in the art of immunoassay.

The methods of the present invention are also useful for the detection of nucleic acids. In one embodiment a method makes use of enzyme-labeled nucleic acid probes. Exemplary methods include solution hybridization assays, DNA detection in Southern blotting, RNA by Northern blotting, DNA sequencing, DNA fingerprinting, colony hybridizations and plaque lifts, the conduct of which is well known to those of skill in the art.

In addition to the aforementioned antigen-antibody, hapten-antibody or antibody-antibody pairs, specific binding pairs also can include complementary oligonucleotides or polynucleotides, avidin-biotin, streptavidin-biotin, hormone-receptor, lectin-carbohydrate, IgG protein A, binding protein-receptor, nucleic acid-nucleic acid binding protein and nucleic acid-anti-nucleic acid antibody. Receptor assays used in screening drug candidates are another area of use for the present methods. Any of these binding pairs can be adapted to use in the present methods by the three-component sandwich technique or the two-component competitive technique described above.

The present invention also contemplates providing kits for performing assays in accordance with the methods of the present invention. Kits may comprise, in packaged combination, chemiluminescent labels as either the free labeling compounds, chemiluminescent labeled specific binding partners, chemiluminescent derivatized solid supports, such as particles or microplates, or chemiluminescent labeled auxiliary substances such as blocking proteins, along with a trigger solution and instructions for use. Kits may optionally also contain activator conjugates, analyte calibrators and controls, diluents and reaction buffers if chemiluminescent labeling is to be performed by the user.

EXAMPLES

Example 1

Synthesis of Compound 1

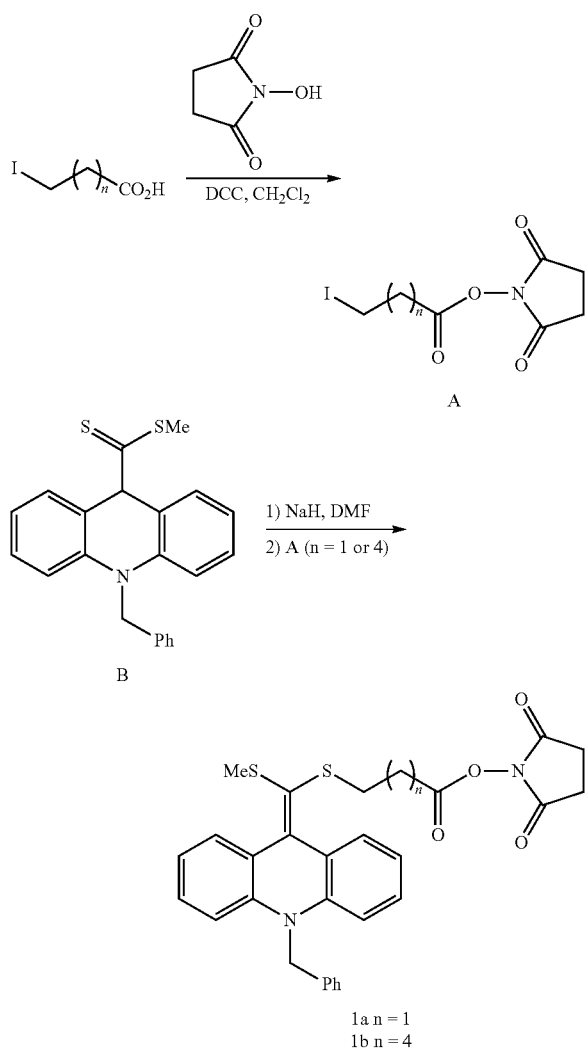

The iodocarboxylate NHS ester was synthesized by reacting the iodocarboxylic acids with N-hydroxysuccinimide using DCC as the coupling reagent. Compound B was prepared using the methods disclosed in US Patent Application Publication 2005/0158815.

To a solution of dithioester B (1.808 g, 5.00 mmol) in anhydrous DMF (50 mL) was added NaH (60% in mineral oil, 0.200 g, 5.00 mmol) under argon. After 4 h at room temperature NHS 3-iodopropionate A (1.485 g, 5.00 mmol) was added and the resulting mixture was stirred overnight. DMF was removed in vacuo. Column chromatography with $CH_2Cl_2$/EtOAc (40:1) afforded 1.770 g of 1 as a yellow solid (yield 67%). $^1$H NMR (400 MHz, $CDCl_3$): δ 2.30 (s, 3H), 2.74 (t, 2H), 2.83 (s, 4H), 3.01 (t, 2H), 5.31 (s, 2H), 6.88 (t, 2H), 7.07 (m, 2H), 7.11-7.18 (m, 3H), 7.27 (m, 4H), 7.82 (dd, 1H), 7.89 (dd, 1H) ppm.

Example 2

Synthesis of Compound 2

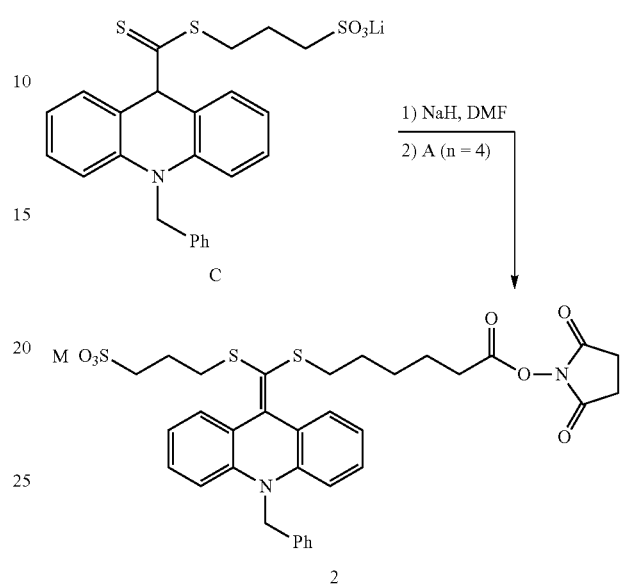

Compound C was prepared using the methods disclosed in US Patent Application Publication 2005/0158815. A mixture of dithioester C (0.692 g, 1.50 mmol) and NaH (60% in mineral oil, 0.060 g, 1.50 mmol) in anhydrous DMF (20 mL) was stirred under argon at room temperature for 4 hours, resulting a slightly cloudy solution. NHS 6 iodohexanoate A (n=4) (0.661 g, 1.95 mmol) in 5 mL of DMF was then added. After 16 h, DMF was removed in vacuo. To the residue was added 10 mL of acetone followed by 20 mL of ether. The supernatant was decanted. The precipitate was washed three times following the same procedure. After drying under vacuum, 1.200 g of 2 was obtained as a yellow solid. $^1$H NMR (400 MHz, $CD_3OD$): δ 1.15 (m, 2H), 1.33-1.47 (m, 4H), 2.01 (p, 2H), 2.38 (t, 2H), 2.67 (t, 2H), 2.75 (t, 2H), 2.82 (s, 4H), 2.88 (t, 2H), 5.32 (s, 2H), 6.88-6.93 (m, 2H), 7.00 (t, 2H), 7.08-7.28 (m, 7H), 7.83 (d, 1H), 7.92 (d, 1H) ppm.

Example 3

Synthesis of Compounds 3 and 4

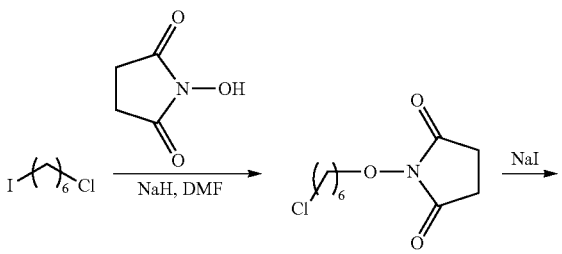

-continued

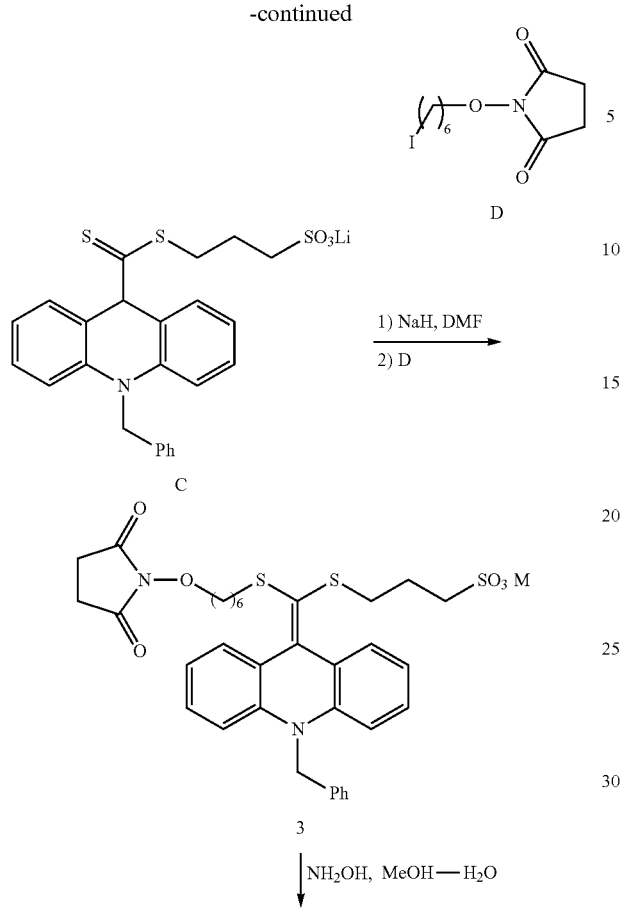

A mixture of dithioester C (1.00 g, 2.10 mmol) and NaH (60% in mineral oil, 0.087 g, 2.16 mmol) in anhydrous DMF (20 mL) was stirred under argon at room temperature for 4 hours, resulting in a slightly cloudy solution. N-6 iodohexoxysuccinimide D (0.82 g, 2.52 mmol) in 5 mL of DMF was then added. The mixture was stirred over night after which DMF was removed in vacuo. The residue was washed four times with 30 mL of ether giving 1.35 g of 3.

Compound 3 (0.25 g) was dissolved in 5 mL of methanol to which was added 5.0 mL of 50% aq. $NH_2OH$. After stirring the solution for 2 days, the solvents were evaporated under vacuum. The residue was washed with 6×20 mL of ether giving 0.21 g of 4. $^1H$ NMR (400 MHz, $CD_3OD$): δ 1.14 (m, 4H), 1.40 (m, 4H), 1.94 (p, 2H), 2.65-2.71 (m, 4H), 2.84 (t, 2H), 3.55 (t, 2H), 5.31 (s, 2H), 6.88 (d, 2H), 6.98 (q, 2H), 7.10 (m, 4H), 7.12-7.27 (m, 3H), 7.85 (t, 2H) ppm.

Example 4

Synthesis of Compounds 5 and 6

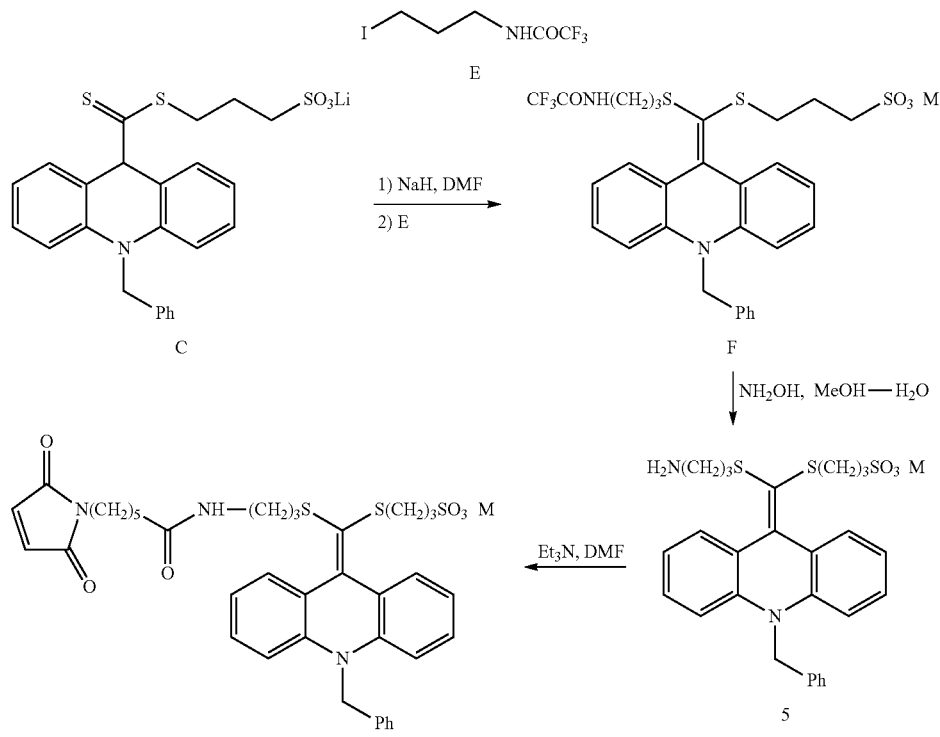

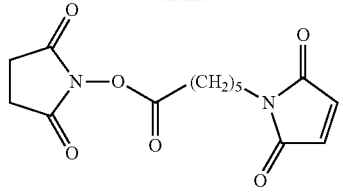

G

A mixture of dithioester C (1.32 g, 2.78 mmol) and NaH (60% in mineral oil, 0.114 g, 2.86 mmol) in 30 mL of anh. DMF was stirred under argon at room temperature for 4 hours. Compound E (1.014 g, 3.61 mmol) in 10 mL of DMF was then added. The mixture was stirred over night after which DMF was removed in vacuo. The residue was washed three times with 20 mL of ether giving 2.10 g of F.

Compound F (2.25 g) was dissolved in a mixture of 15 mL of 7 N $NH_3$ in MeOH and 10 mL of 28% aqueous ammonia. After 3 days of stirring, solvents were removed under vacuum. The residue was washed with ether (3×50 mL) and recrystallized with $H_2O$/2-propanol, giving 1.20 g of 5.

To a suspension of 5 (0.300 g, 0.563 mmol) in 9.0 mL of dry DMF was added 1.20 mL of triethylamine. The mixture was stirred for 5 min, giving a slightly cloudy solution. To this was added 6-maleimidohexanoic NHS ester (G 0.260 g, 0.843 mmol). A clear solution resulted in 5 min. After 16 hrs, DMF was removed under vacuum. The residue was washed with ether (4×30 mL), then dissolved in MeOH (2 mL) and precipitated with ether (50 mL). A 0.400 g yield of 6 was obtained as a yellowish foam-like solid. $^1$H NMR (400 MHz, $CD_3OD$): δ 1.26 (t, 11H), 1.49-1.58 (m, 6H), 1.90 (p, 2H), 2.08 (t, 2H), 2.68 (m, 4H), 2.80 (t, 2H), 3.00 (t, 2H), 3.15 (q, 6H), 3.42 (t, 2H), 5.28 (s, 2H), 6.73 (s, 2H), 6.85 (d, 2H), 6.96 (m, 2H), 7.07 (m, 4H), 7.18-7.25 (m, 3H), 7.83 (m, 2H) ppm.

Example 5

Additional Labeling Compounds 7-12

The preparation of other exemplary labeling compounds listed below was disclosed in U.S. Pat. No. 6,858,733.

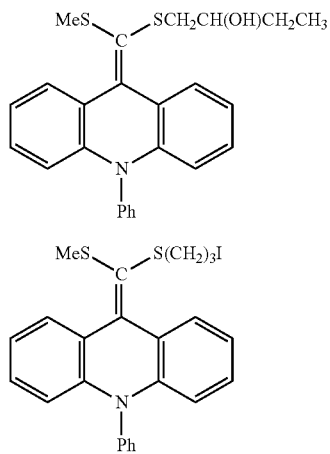

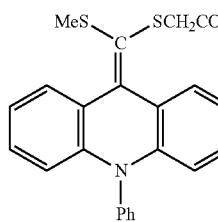

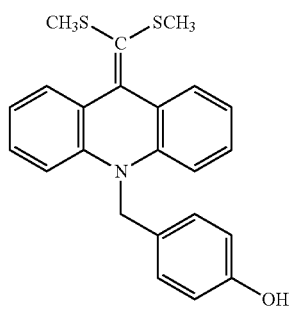

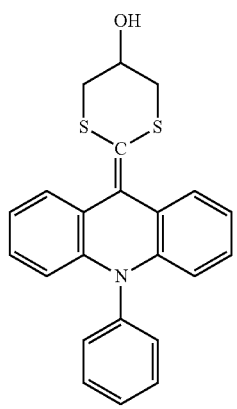

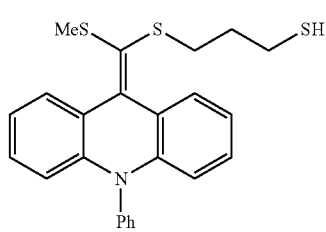

Example 6

Additional Labeling Compounds

Compounds 13 and 14 were prepared by a similar reaction sequence as was used in preparing 1 but starting with N-methylacridan and N-phenylacridan, respectively. In these structures M represents a positively charged counter ion, such as Li⁺ or Na⁺.

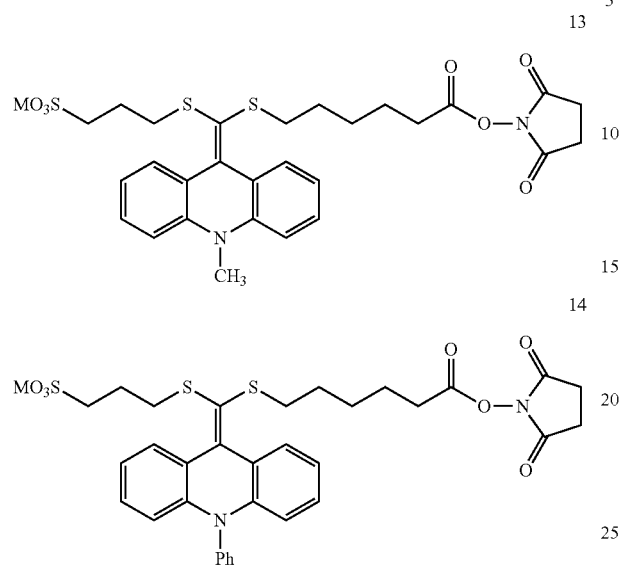

Example 7

Preparation of Labeling Compound 15

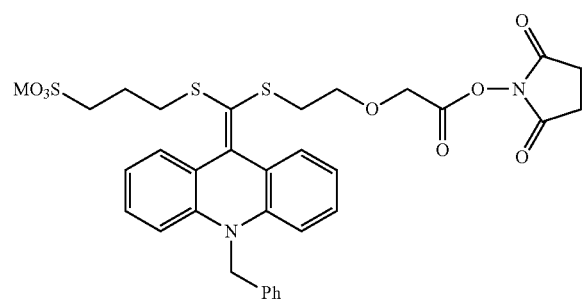

Compound C of Example 4 after formation of the enethiolate anion with NaH in DMF, was S-alkylated with iodo NHS ester H. The product was purified by recrystallization from 2-propanol.

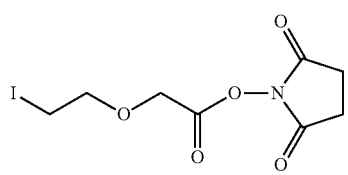

Example 8

Preparation of Acridan-labeled Antibody. The acridan labeling compound 3 of example 3 was used to label sheep anti-mouse IgG (H+L) (Jackson Immunoresearch). A solution of 0.24 mg of the antibody in 0.1 M borate buffer, pH 8.25 and compound 3 in 500 µL of DMF (10:1 molar ratio 3:antibody) was reacted for 15 min at room temperature and then at 4° C. over night. The solution was passed through a desalting column (BioRad) eluted with PBS buffer to remove unbound label. Labeled antibody along with any unreacted antibody was obtained by collecting 500 µL fractions.

The fractions were tested for the amount of labeled antibody by a chemiluminescent assay. A 1 or 10 µL aliquot was mixed with 50 µL of 0.4 M HCl+3.6% urea peroxide, followed by injection of 50 µL of 0.5 M NaOH in a tube in a Turner Designs TD-20e luminometer. The total integrated intensity from the burst of luminescence was measured from the time of injection. Those fractions showing chemiluminescence were retained. Fraction 8 contained the maximal amount of product.

Example 9

Preparation of Acridan-labeled BSA. The acridan labeling compound 3 of example 3 was used to label bovine serum albumin (BSA). A solution of 0.1 g of BSA in 500 µL of 0.1 M borate buffer, pH 8.25 and 42 µL of a solution containing 23.4 mg compound 3 in 100 µL DMF (10:1 molar ratio 3:BSA) was reacted for 15 min at room temperature and then at 4° C. over night. The solution was passed through a desalting column (BioRad) eluted with PBS buffer to remove unbound label. Labeled BSA along with any unreacted BSA was obtained by collecting 500 µL fractions.

The fractions were tested for the amount of labeled BSA by the chemiluminescent assay of example 8. Those fractions showing chemiluminescence were retained. Fraction 7 contained the maximal amount of product.

Example 10

Preparation of Acridan Functionalized Microwells. White polystyrene 96-well microplates functionalized with carboxylic acid groups (Biosystems) are coupled with compound 5 using EDC as coupling agent. A stock solution of compound 5 in a 70:30 (v/v) solution of DMF and 0.1 M MES buffer, pH 4 is prepared. A 0.2 mL aliquot was added to each well of the plate that had been previously washed in MES buffer. EDC in MES buffer is added and the mixture reacted over night. The supernatant is removed and the wells washed sequentially twice with water and six times with methanol.

Example 11

Preparation of Acridan-Labeled Poly(Methacrylate) Microparticles

Amberlite resin (IRP-64, 100-400 mesh, 2.50 g) was reacted with SOCl₂ at reflux for four hours. The reaction was cooled and the volatiles removed under vacuum. The beads were then suspended in 50 mL of CH₂Cl₂ to which 17.0 mL of triethylamine was added followed by 15.0 mL of ethylenediamine. The mixture was stirred under Ar over night. The particles were dispersed by addition of 100 mL of MeOH and then filtered. The filtered particles were washed with MeOH and CH₂Cl₂ and then air dried. The resulting particles weighed 2.80 g for a calculated NH₂ content of 2.86 mmol/g.

The ethylenediamine-modified particles, 100 mg in 10 mL of anhydrous DMF, were stirred under Ar with 10 mg of compound 2 at room temperature over night. The mixture was filtered and the particles washed with MeOH. After air-drying, the recovered functionalized particles weighed 102 mg.

In an alternate method, 2.50 g of Amberlite resin was converted to the acid chloride form by reaction with $SOCl_2$ as above, and then reacted with 4.32 g of N-hydroxysuccinimide in 50 mL of THF and 6.8 mL of triethylamine to prepare the NHS ester-functionalized particles. These were reacted with compound 5 containing a free terminal $NH_2$ group to effect coupling.

Example 12

Conjugation of Acridan-Labeled Microparticles with Antibody

A 20 mg quantity of the Acridan-labeled Amberlite particles of example 11, containing unreacted terminal $NH_2$ groups, was further reacted with 102 mg of disuccinimidyl octanedioate, (~5 eq.) in 1 mL of anh. DMF for 15 min at room temperature. The particles were separated by centrifugation and washed with 10×1 mL of DMF. The resulting free NHS ester was coupled to sheep anti-mouse IgG (0.5 mL of a stock 1.8 mg/mL solution) in 0.1 M borate buffer, pH 8.5, 2 mM EDTA over night at 4° C. The reaction mixture was centrifuged at 13 k rpm and the supernatant removed. The particles were washed several times on a spin column with PBS+ 0.05% Tween-20.

The resulting antibody-labeled particles were blocked with BSA by incubation in 1.0 mL of blocking buffer (1% BSA, 1% sucrose in 1×PBS) at 37° C. for 1 hour. The particles were washed with Tween-PBS wash buffer and stored in 1.0 mL of 1×PBS.

Example 13

Preparation of Acridan-Labeled Magnetic Microparticles. A stock solution of 4 mg of compound 5 in a solution of 0.7 mL of DMF and 0.3 mL of 0.1 M MES buffer, pH 4 was prepared. A 0.1 mL aliquot was added to 50 mg of carboxylated polystyrene particles (Dynal Dynabeads M-270 carboxylic acid), which had been washed in MES buffer. The mixture was diluted with 0.67 mL of MES buffer and 0.23 mL of DMF. EDC (23 mg) was added and the mixture shaken over night. The supernatant was removed and the particles washed sequentially with 2×1 mL of water and 6×1 mL of MeOH and resuspended in 1 mL of MeOH.

The particles were tested for label incorporation. A 10 μL aliquot (containing ca. 0.5 mg of particles) was added to 0.5 mL of water to prepare a 1 mg/mL stock. A 100 μL aliquot was reacted with an excess of HRP for 5 min. The particles were washed with 4×1 mL of water and then suspended in 1 mL of water. Trigger solution 1 (10 μL) containing 25 mM tris, pH 8.0, 8 mM p-hydroxycinnamic acid, 1 mM EDTA, 0.2% Tween-20 and 0.1 M urea peroxide was injected and the flash of chemiluminescence recorded in a luminometer. A signal of 6040 RLU was observed compared to a blank of 18 RLU.

A 5 mg portion of particles was washed with 2×200 μL of 0.1 M MES buffer, pH 4 and then resuspended in 117 μL of MES buffer. Sheep anti-mouse IgG (0.15 mg from a stock 1.8 mg/mL solution) was added to the particles and the mixture was shaken for 30 minutes. EDC, 5 mg, was added and the mixture was shaken for 4 hours. The supernatant was removed and the beads were washed with 3×500 μL of PBS-T (PBS+0.05% Tween-20).

The particles were resuspended in 500 μL of blocking buffer (PBS+1% BSA+1% sucrose) and 5 mg of EDC, stirred for 15 min at room temperature and stirred at 4° C. over night. The supernatant was removed and the particles washed with 2×500 μL of PBS-T and resuspended in 1 mL of PBS.

Example 14

Microplate Immunoassay Using Labeled Capture Antibody. The product-containing fraction from the preparation of labeled antibody in example 8 was diluted 1:100 in PBS buffer. A 50 μL aliquot was added to each of 26 wells of a white polystyrene 96 well plate. The plate was agitated for 5 minutes at room temperature on an orbital shaker. The solution was removed and the wells washed three times with PBS-T, removing all wash buffer after each step.

Sheep anti-mouse IgG $F(ab^1)_2$-HRP conjugate (Jackson Immunoresearch) was diluted $1:1.2\times10^6$ in a conjugate buffer comprising 2.5% BSA and 1% sucrose in 1×PBS. Alternatively, the conjugate could also be diluted in other matrices such as FBS. Aliquots of diluted conjugate were dispensed into the 26 wells. IgG standards containing from 100 ng/mL- 0.048 ng/mL were prepared by 2-fold dilution along with a 0 ng/mL solution in anti-IgG $F(ab^1)_2$-HRP conjugate solution. The standards and zero were dispensed into wells achieving a final volume 50 μL/well. The plate was incubated 1 hr at room temperature on the plate shaker.

Figure 4:
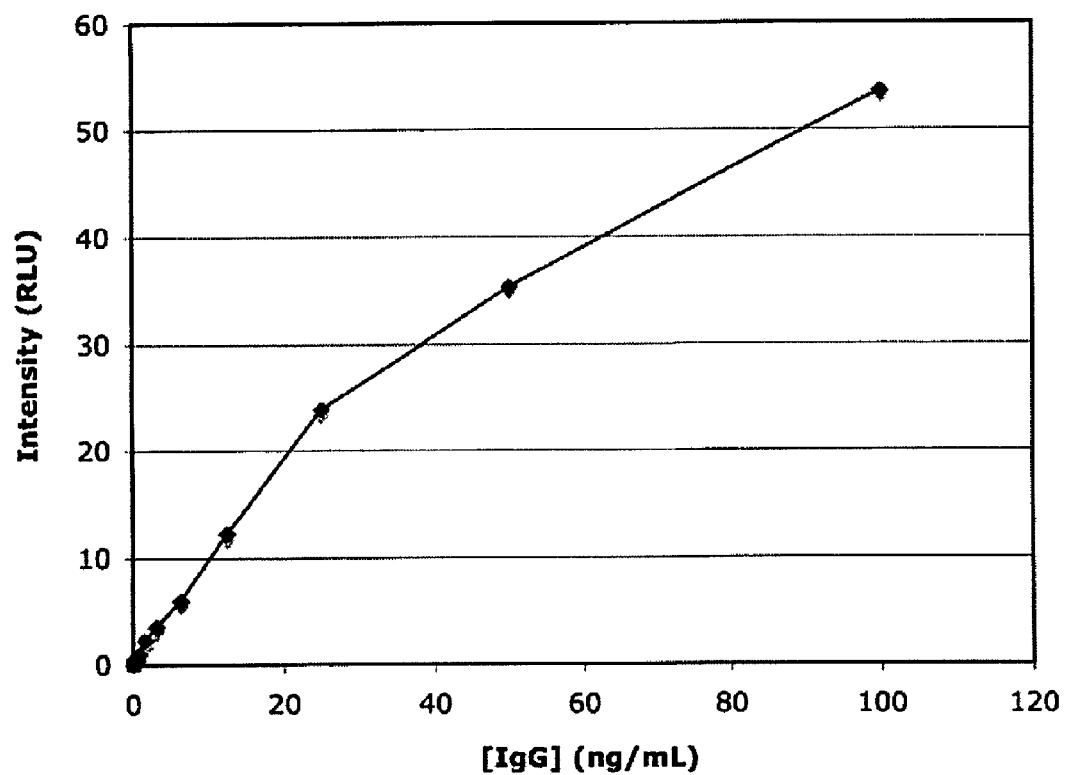
FIG. 4 is a graph showing detection of IgG antigen in a nonseparation immunoassay using a labeled capture antibody immobilized in the wells of a microplate and excess anti-IgG-HRP conjugate for detection.

The plate was transferred to a Luminoskan plate luminometer. Without removing the conjugate solution, luminescence was generated by sequentially injecting 100 μL of trigger solution 1, and reading the integrated intensity in each well for 5 seconds. A plot of the resulting assay is shown in FIG. 4. The assay allowed quantitation over the entire range tested with the lowest calibrator exceeding the signal of the zero+2 standard deviations of the zero.

Example 15

Microplate Immunoassay Unlabeled Capture Antibody and Labeled BSA. A 50 μL aliquot of unlabeled sheep anti-mouse IgG (H+L), 40 μg/mL of 1×PBS, was added to coat each of 26 wells of a white polystyrene 96 well plate. The plate was agitated for 5 minutes at room temperature on an orbital shaker. The solution was removed and the wells washed three times with PBS-T, removing all wash buffer after each step.

The product-containing fraction from the preparation of labeled BSA in example 9 was diluted to 50 μL/mL with PBS buffer+1% sucrose. A 100 μL aliquot was added to each of the 26 wells of the white polystyrene 96 well plate. The plate was held for 1 hr at 37° C. The solution was removed and the wells washed three times with PBS-T, removing all wash buffer after each step.

Sheep anti-mouse IgG $F(ab^1)_2$-HRP conjugate was diluted $1:1.2\times10^6$ in a conjugate buffer comprising 1% BSA and 1% sucrose in 1×PBS. Aliquots of diluted conjugate were dispensed into the 26 wells. IgG standards containing from 100 ng/mL-0.048 ng/mL were prepared by 2-fold dilution along with a 0 ng/mL solution in anti-IgG $F(ab^1)_2$-HRP conjugate solution. The standards and zero were dispensed into wells achieving a final volume 50 μL/well. The plate was incubated 1 hr at room temperature on the plate shaker.

Figure 5:
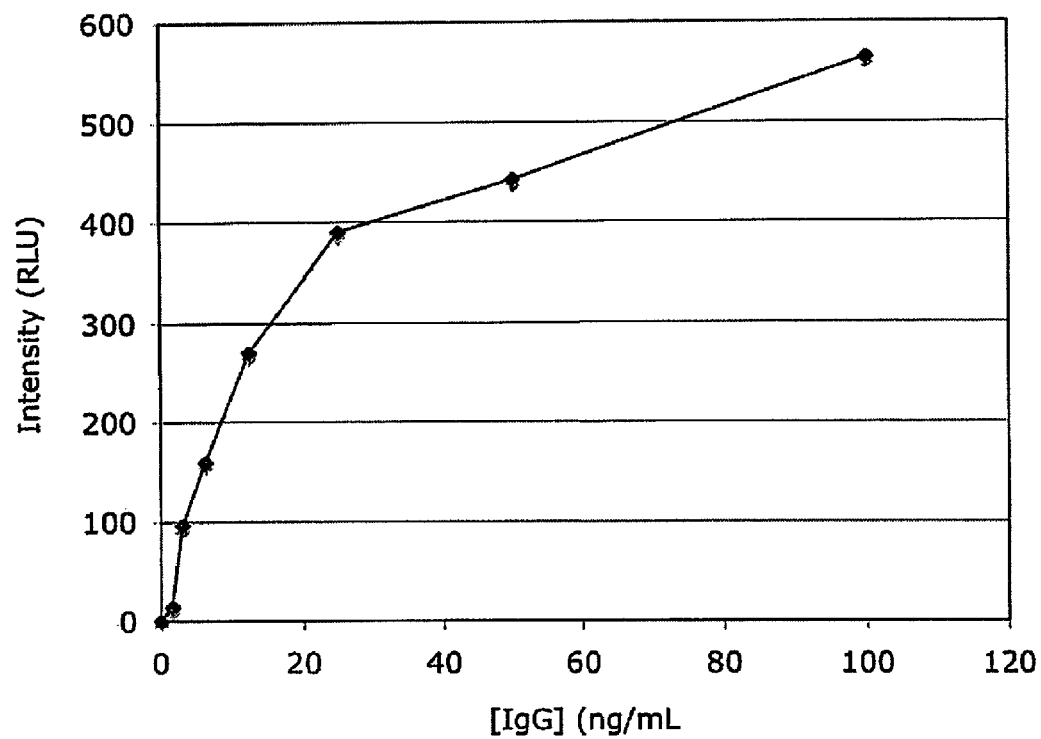
FIG. 5 is a graph showing detection of IgG antigen in a nonseparation immunoassay conducted according to the invention using labeled blocking protein and an unlabeled capture antibody immobilized in the wells of a microplate and excess anti-IgG-HRP conjugate for detection.

The plate was transferred to a Luminoskan plate luminometer. Without removing the conjugate solution, luminescence was generated by sequentially injecting 100 μL of trigger solution 1, and reading the integrated intensity in each well for 5 seconds. A plot of the resulting assay is shown in FIG. 5. The assay allowed quantitation over the entire range tested with the lowest calibrator exceeding the signal of the zero+2 standard deviations of the zero.

In a control experiment, removing the solution from a well and analysis of the solution showed that light emission originated from the surface of the well and not from the solution.

Example 16

Microparticle Immunoassay Using Labeled Magnetic Microparticles

A quantity of Acridan and antibody co-labeled magnetic microparticles of example 13 sufficient to provide 50 µg per reaction was washed three times with PBS-T and resuspended in sheep anti-mouse IgG F(ab$^1$)$_2$-HRP conjugate diluted 1:1.2×10$^6$ in 1×PBS buffer containing 1% BSA and 1% sucrose. The particle suspension was dispensed into 26 wells of a white polystyrene 96 well plate. IgG standards in sheep anti-mouse IgG F(ab$^1$)$_2$-HRP conjugate solution were prepared by 2-fold serial dilution to result in final concentrations of 100 ng/mL-0.048 ng/mL or 0 ng/mL in the wells. The respective standards and zero were dispensed into wells to make a final reaction volume of 50 µL/well. The plate was incubated for 1 hr at room temperature on a plate shaker.

The plate was transferred to a Luminoskan plate luminometer. Without removing the conjugate solution, luminescence was generated by sequentially injecting 100 µL of trigger solution 1, and reading the integrated intensity in each well for 5 seconds. A plot of the resulting assay allowed quantitation of IgG.

Example 17

Microparticle Immunoassay Using Labeled Amberlite Microparticles

A quantity of Acridan and antibody co-labeled magnetic microparticles of example 13 sufficient to provide 100 µg per reaction was washed three times with PBS-T and resuspended in sheep anti-mouse IgG F(ab$^1$)$_2$-HRP conjugate diluted 1:1.2×10$^6$ in 1×PBS buffer containing 1% BSA and 1% sucrose. The particle suspension was dispensed into 26 wells of a white polystyrene 96 well plate. IgG standards in sheep anti-mouse IgG F(ab$^1$)$_2$-HRP conjugate solution were prepared by 2-fold serial dilution to result in final concentrations of 100 ng/mL-0.048 ng/mL or 0 ng/mL in the wells. The respective standards and zero were dispensed into wells to make a final reaction volume of 50 µL/well. The plate was incubated for 1 hr at room temperature on a plate shaker.

The plate was transferred to a Luminoskan plate luminometer. Without removing the conjugate solution, luminescence was generated by sequentially injecting 100 µL of trigger solution 1, and reading the integrated intensity in each well for 5 seconds. A plot of the resulting assay allowed quantitation of IgG.

Example 18

Preparation of Acridan-Labeled Carboxyl-Modified Microparticles. Carboxylic acid-modified polystyrene 1 µm microparticles (Seradyn) having a carboxyl loading of 0.0282 meq/g were conjugated to compound 5 by EDC coupling according to the procedure described in example 13. A 52.5 mg portion of particles (1.48 µmol COOH) was treated with 0.39 mg of 5 (0.74 µmol) to ensure that some unreacted COOH groups remained. The free COOH groups were coupled to sheep ant-mouse IgG (1.48 µmol) by EDC coupling in pH 4 MES buffer. Unreacted antibody was removed by washing with PBS-T buffer using a spin column.

Example 19

Preparation of Acridan-Labeled Modified Magnetic Silica Microparticles. Commercially obtained magnetite (10.0 g) having a particle size range of 1-5 µm was coated by a Stöber process with a mixture of tetraethylorthosilicate (27.0 g) and 3-aminopropyl-triethoxysilane (3.0 g). An additional coating with 3.75 g of 3-aminopropyltriethoxysilane was performed subsequently.

The aminopropylsilane-modified magnetic silica particles were reacted with compound 2 of example 2 as follows. A 25 mg portion of the aminopropyl-functionalized magnetic particles was mixed with 1 mL of DMF in a 1.5 mL centrifuge tube. A 5 µL aliquot of a 1 mg/mL solution of compound 2 in DMF was added to the particle suspension and the mixture agitated on a shaker over night. The supernatant was removed on a magnetic rack and the particles washed sequentially with several portions of methanol followed by several portions of DMF.

Example 20

TSH Sandwich Immunoassay using Acridan-Labeled Modified Magnetic Silica Microparticles. The acridan-labeled particles of example 19 were covalently linked to a mouse anti-TSH antibody by activating the particles with a solution of 128 mg of the homobifunctional linker disuccinimidyloxysuberate (DSS) in 1.2 mL of DMF for 25 minutes. The supernatant was removed on a magnetic rack and the particles washed with DMF.

The activated particles were coupled to antibody by adding a solution of 0.225 mg of antibody in 0.1 M borate buffer, pH 8.25 and shaking the mixture for 45 minutes before storing at 4° C. over night. The resulting antibody-coated particles were washed with PBS-T and then blocked in PBS buffer containing 1% BSA and 1% sucrose for 1 hr at 37° C. The particles were washed in PBS-T buffer, followed by washing with PBS and stored as a 20 mg/mL suspension in PBS buffer.

A white polystyrene microplate was employed to contain the particles and a provide reaction vessel for the immunoassays. The wells were blocked before use with PBS buffer containing 1% BSA and 1% sucrose (1% Block) and washed with PBS-T. A 1 mg/mL stock solution of goat anti-TSH-HRP conjugate (signal antibody) was diluted 1:15,000 in 1% Block. A TSH standard stock solution having a concentration of 100 µIU/mL was serially diluted in 1:2 dilutions down to 0.00076 µIU/mL. Particles were separated from storage buffer and resuspended in HRP conjugate solution. Aliquots of particle suspension containing 0.1 mg of particles were added to a sufficient number of wells to permit duplicate assays over the desired concentration range, typically 12.5-0.0020 µIU/mL. TSH standards were dispensed in the well. A blank comprising 1% Block or fetal bovine serum (FBS) was added to duplicate wells. The plate was covered with a plate sealer and incubated with agitation at 37° C. for 1 hour. Luminescence was read by injecting trigger solution 2 and measuring light for 2 or 5 seconds in a sequential manner. Trigger solution 2 contained 25 mM tris, pH 8.0, 8 mM p-hydroxycinnamic acid, 1 mM EDTA, 0.2% Tween-20 and 5 mM urea peroxide.

| TSH Conc. μIU/mL | Signal-Blank |
| --- | --- |
| 12.5 | 196.5 |
| 6.25 | 140.9 |
| 3.13 | 88.3 |
| 1.56 | 47.4 |
| 0.78 | 24.1 |
| 0.39 | 11.5 |
| 0.20 | 6.39 |
| 0.097 | 3.46 |
| 0.048 | 2.02 |

Example 21

Preparation of Acridan-Labeled Modified Polystyrene Microparticles. Dynal M-270 amine-functionalized polystyrene microparticles were functionalized with acridan labeling compound 2 and mouse anti-TSH antibody as described in examples 19 and 20.

Example 22

TSH Sandwich Immunoassay using Acridan-Labeled Modified Polystyrene Particles. The particles of example 21 were used to conduct a sandwich immunoassay for TSH according to the general protocol of example 20.

| TSH Conc. μIU/mL | Signal-Blank |
| --- | --- |
| 12.5 | 588.6 |
| 6.25 | 303.6 |
| 3.13 | 149.7 |
| 1.56 | 68.43 |
| 0.78 | 30.66 |
| 0.39 | 13.89 |
| 0.20 | 6.95 |
| 0.097 | 3.31 |
| 0.048 | 1.50 |
| 0.024 | 0.925 |

Example 23

Preparation of Acridan-Labeled Modified Polystyrene Microparticles. Dynal M-270 amine-functionalized magnetic polystyrene microparticles were functionalized with acridan labeling compound 2 as follows. An aliquot of the particle suspension was removed, the supernatant decanted, and the particles washed sequentially with water, acetonitrile and DMF. A 25 mg portion of the particles was mixed with 1 mL of DMF in a 1.5 mL centrifuge tube. A 5 μL aliquot of a 1 mg/mL solution of compound 2 in DMF was added to the particle suspension and the mixture agitated on a shaker over night. The supernatant was removed on a magnetic rack and the particles washed sequentially with several portions of methanol followed by several portions of DMF.

Biotin-NHS ester, 250 μL of a 1 mg/mL solution in DMF, was added to 12.5 mg of the above particles in 1 mL of DMF. The mixture was vortexed for 30 s and agitated on a shaker over night. The supernatant was removed and the particles washed with DMF and then with PBS buffer.

Streptavidin, 200 μg in 1 mL of PBS, was added to the particles, the mixture vortexed for 1 min, and then agitated on a shaker at 37° C. for 1 h. The supernatant was removed and the particles washed with PBS-Tween buffer and then blocked in PBS buffer containing 1% BSA and 1% sucrose for 1 hr at 37° C. The particles were washed in PBS-Tween buffer, followed by washing with PBS.

The particle suspension in PBS was reacted with 14 μg of biotinylated sheep anti-mouse TSH antibody at 37° C. for 1 h. The supernatant was removed and the particles washed with PBS-Tween buffer, followed by washing with PBS. The resulting particles were resuspended in PBS at a concentration of 20 mg/mL.

Example 24

Alternate Preparation of Acridan-Labeled Modified Polystyrene Microparticles

Dynal M-270 amine-functionalized magnetic polystyrene microparticles were functionalized with acridan labeling compound 2 as in the previous example. Biotin was conjugated to the particles using the commercially available compounds, designated biotin-PEG 4-NHS and biotin-PEG 12-NHS.

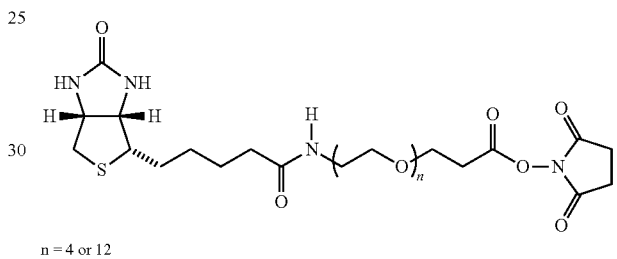

n = 4 or 12

All subsequent steps, i.e., binding of streptavidin and biotinylated sheep anti-mouse TSH antibody, were conducted as described in the previous example.

Example 25

TSH Sandwich Immunoassay using Polystyrene Particles of Example 24

The particles of example 24, prepared using biotin-PEG 12-NHS, were used to conduct a sandwich immunoassay for TSH. A white polystyrene microplate was employed to contain the particles and a provide reaction vessel for the immunoassays. The wells were blocked before use with 1% Block and washed with PBS-T. A 1 mg/mL stock solution of goat anti-TSH-HRP conjugate (signal antibody) was diluted 1:15, 000 in 1% Block. A TSH standard stock solution having a concentration of 100 μIU/mL was serially diluted in 1:2 dilutions down to 0.00076 μIU/mL in FBS. Particles were separated from storage buffer and resuspended in HRP conjugate solution. Aliquots of particle suspension containing 0.05 mg of particles were added to a sufficient number of wells to permit duplicate assays over the desired concentration range, typically 12.5-0.002 μIU/mL. TSH standards were dispensed in the well. A blank comprising 1% Block or FBS was added to duplicate wells. The plate was covered with a plate sealer and incubated with agitation at 37° C. for 1 hour. Luminescence was read by injecting trigger solution 2 and measuring light for 2 or 5 seconds in a sequential manner.

| TSH Conc. µIU/mL | Signal-Blank |
|---|---|
| 12.5 | 492.3 |
| 6.25 | 291.7 |
| 3.13 | 147.4 |
| 1.56 | 72.07 |
| 0.78 | 32.21 |
| 0.39 | 14.31 |
| 0.20 | 7.04 |
| 0.097 | 3.34 |
| 0.048 | 1.90 |
| 0.024 | 0.655 |

Nearly identical results were obtained in an assay using the particles of example 24, prepared using biotin-PEG 4-NHS.

Example 26

Additional lots of particles of the type described in example 19 were prepared according to the synthetic method described, but with the following variations.

1. The magnetite was coated with the following ratios of tetraethylorthosilicate to 3-aminopropyltriethoxysilane: 97.5:2.5, 95:5, 90:10, 80:20, and 60:40 with no additional coating of 3-aminopropyltriethoxysilane.

2. The coated magnetite, 25 mg, was reacted with the following loadings of compound 2: 125 µg, 12.5 µg, 5 µg, and 2.5 µg.

3. Particles prepared using 5 and 2.5 µg of compound 2 were coated with 0.45 mg, 0.225 mg, or 0.1125 mg of anti-mouse TSH antibody.

4. The coated magnetite, 25 mg, was reacted with 5 µg of compound 1b.

All lots of particles were successfully used to perform a TSH sandwich immunoassay according to the methods described above.

Example 27

Preparation of a Biotin-Acridan Conjugate

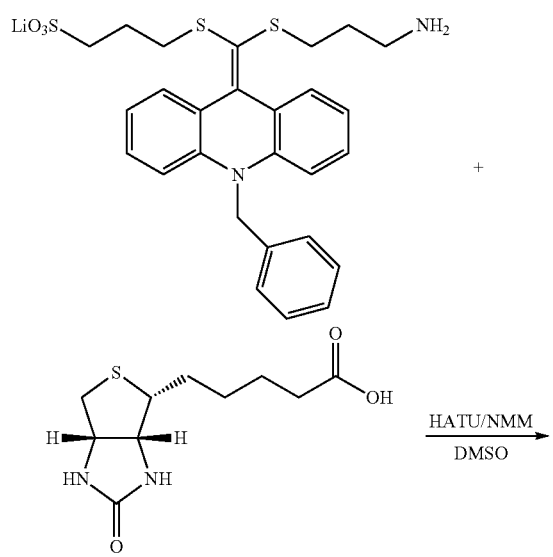

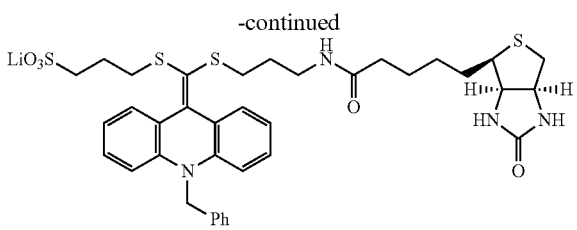

A 100 mL round bottom flask was charged with 430 mg (0.82 mmol) of acridan compound and 250 mg (1 mmol) of biotin, 15 mL of DMSO, and 0.45 mL of 4-methyl-morpholine (NMM) at room temperature. The mixture was stirred for 30 min until all solids were dissolved. Then 380 mg of HATU (Aldrich cat. No. 44, 546-0) was added in one portion and stirring continued overnight. DMSO was diluted with 30 mL of ether causing separation of a gel. The solvent was decanted and the gel washed with ether several times. The resulting gel-like mixture was dissolved in MeOH and purified by flash chromatrography, eluting with 10% MeOH/CH$_2$Cl$_2$ yielding 250 mg (32%). $^1$H NMR (400 MHz, DMSO-d$_6$): δ 7.85-7.81 (m. 2H), 7.28-6.83 (m, 11H), 5.26 (s, 2H), 4.4 (m 1H), 4.2 (s, 1H), 3.2-3.0 (m, 4H), 2.82-2.76 (m, 3H), 2.70-2.55 (m, 5H), 2.15 (m, 2H), 1.88-1.82 (m, 2H), 1.63-1.50 (m, 6H), 1.41-1.38 (m, 2H) ppm.

Example 28

Figure 8:
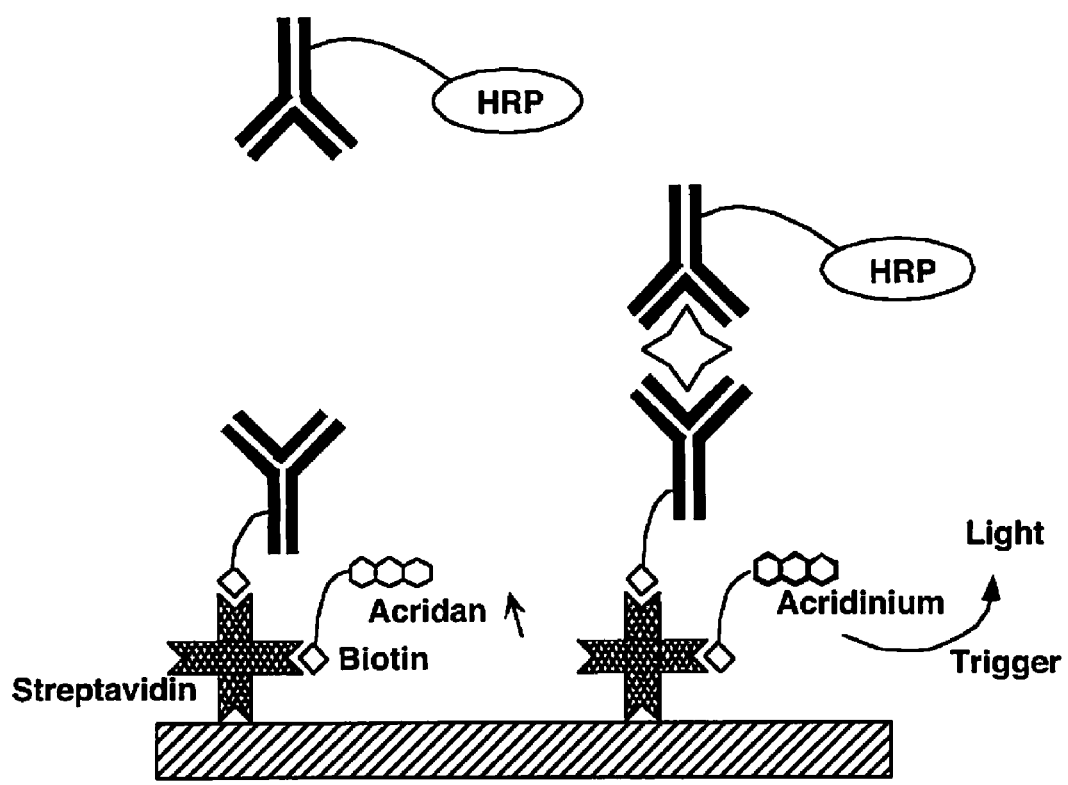
FIG. 8 is a schematic diagram of the detection step of another immunoassay conducted according to the invention making use of biotin-avidin binding to create a labeled solid surface and having label and capture antibody held in proximity.
Figure 9:
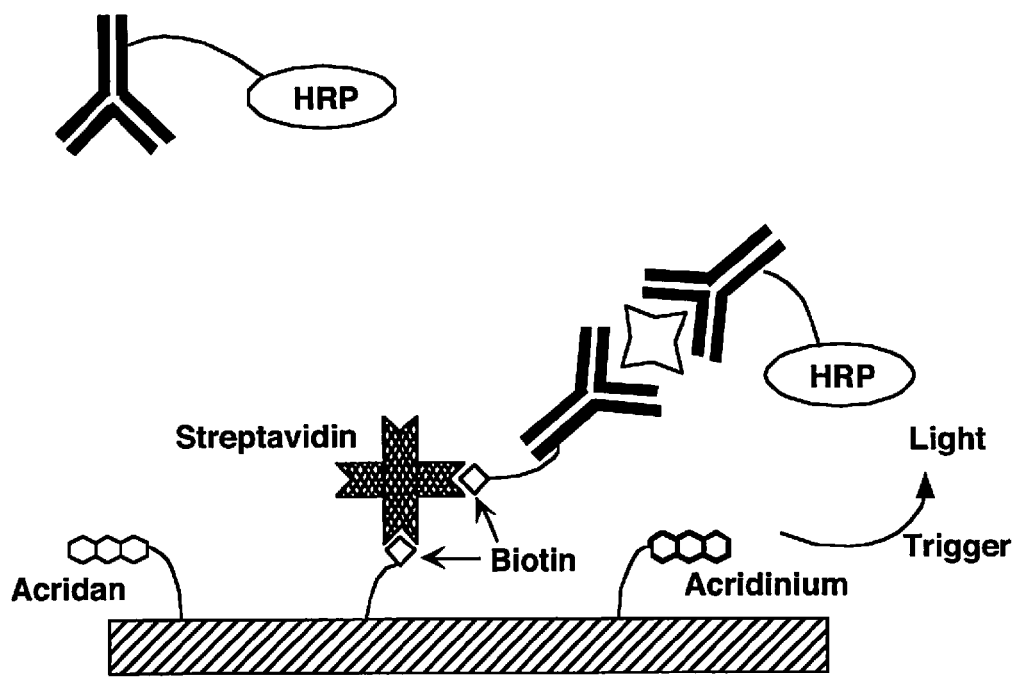
FIG. 9 is a schematic diagram of the detection step of another immunoassay conducted according to the invention also making use of biotin-avidin binding to create a labeled solid surface and having label and capture antibody held in proximity.

Microplate Immunoassay using Streptavidin and Biotin-Acridan Conjugate. An assay was conducted according to the format depicted in FIG. 8. A 100 µL aliquot of streptavidin at 15 µg/mL in 1×PBS was added to coat the wells of a white polystyrene 96 well plate. The plate was agitated for 1 h at room temperature on an orbital shaker. The solution was removed and the wells washed three times with PBS-T, removing all wash buffer after each step.

A 200 µL aliquot of PBS buffer containing 1% BSA and 1% sucrose (1× block) was added to the wells of a white polystyrene 96 well plate. The plate was held for 1 hr at 37° C. The solution was removed and the wells washed three times with PBS-T, removing all wash buffer after each step.

Portions of a solution of biotin-acridan compound of example 27 in 1× block containing 1.5 equivalents of biotin were added to each well. The plate was agitated for 1 h at room temperature on an orbital shaker. The solution was removed and the wells washed three times with PBS-T, removing all wash buffer after each step.

Biotin-conjugated mouse anti-human TSH conjugate (2.45 mg/mL) was diluted 1:20,000 in 1× block. Aliquots, 100 µL, of diluted conjugate were dispensed into the wells. The plate was agitated for 1 h at room temperature on an orbital shaker. The solution was removed and the wells washed three times with PBS-T, removing wash buffer after each step.

TSH standards containing from 12.5 µIU/mL-0.048 µIU/mL were prepared by 4-fold dilution along with a 0 µIU/mL solution in anti-TSH-HRP conjugate solution. The standards and zero were dispensed into wells achieving a final volume 50 µL/well Goat anti-human TSH-HRP conjugate (signal antibody) was diluted 1:30,000 in 1% Block. A 50 µL aliquot of signal antibody and TSH dilution was added to each well and the plate incubated 1 h at 37° C.

The plate was transferred to a Luminoskan plate luminometer. Without removing the conjugate solution, luminescence was generated by sequentially injecting 100 μL of trigger solution 2, and reading the integrated intensity in each well for 5 seconds.

| TSH Conc. μIU/mL | Signal-Blank |
|---|---|
| 12.5 | 535.95 |
| 3.13 | 181.65 |
| 0.78 | 69.57 |
| 0.20 | 40.58 |
| 0.048 | 33.60 |
| 0.012 | 31.46 |
| 0.0 | 29.82 |

Example 29

Control Experiment excluding Signal Antibody. The immunoassay protocol of example 28 was modified by excluding the HRP-conjugated signal antibody.

| TSH Conc. μIU/mL | Signal-Blank |
|---|---|
| 12.5 | 0.727 |
| 3.13 | 0.189 |
| 0.78 | 0.079 |
| 0.20 | 0.023 |
| 0.048 | 0.027 |
| 0.012 | 0.023 |

The level of chemiluminescence detected was essentially at the level of assay background signal demonstrating the necessity of having the activator conjugate bound in proximity to the immobilized chemiluminescent compound.

Example 30

Investigation of Additional Trigger Solution Compositions

The effectiveness of different trigger solutions was assessed in a model immunoassay system. The protocol of example 20 was performed using samples containing either 6.25 μIU/mL (signal) or 0 μIU/mL (blank) of TSH.

| Enhancer | Concentration | Peroxide | Concentration | S/B |
|---|---|---|---|---|
| p-hydroxycinnamic acid | 8 mM | Urea peroxide | 5 mM | 6.5 |
| p-hydroxycinnamic acid | 80 μM | Urea peroxide | 5 mM | 8.1 |
| p-hydroxycinnamic acid | 32 μM | Urea peroxide | 5 mM | 9.6 |
| p-hydroxycinnamic acid | 16 μM | Urea peroxide | 5 mM | 10.9 |
| p-hydroxycinnamic acid | 11 μM | Urea peroxide | 5 mM | 10.2 |
| p-hydroxycinnamic acid | 8 μM | Urea peroxide | 5 mM | 9.8 |

The above data illustrate that various concentrations of enhancer can be used in the trigger solutions of the present invention.

Example 31

Investigation of Additional Trigger Solution Compositions

The effectiveness of different trigger solutions was assessed in a model immunoassay system. The protocol of example 20 was performed using samples containing either 6.25 μIU/mL (signal) or 0 μIU/mL (blank) of TSH.

| Enhancer | Concentration | Peroxide | Concentration | S/B |
|---|---|---|---|---|
| p-hydroxycinnamic acid | 8 μM | Urea peroxide | 10 mM | 5.3 |
| p-hydroxycinnamic acid | 8 μM | Urea peroxide | 25 mM | 5.3 |
| p-hydroxycinnamic acid | 8 μM | Urea peroxide | 37.5 mM | 5.0 |
| p-hydroxycinnamic acid | 8 μM | Urea peroxide | 50 mM | 5.1 |
| p-hydroxycinnamic acid | 8 μM | Urea peroxide | 100 mM | 4.1 |

The above data illustrate that various concentrations of peroxide can be used in the trigger solutions of the present invention.

Example 32

Investigation of Additional Trigger Solution Compositions

The effectiveness of different trigger solutions was assessed in a model immunoassay system. The protocol of example 20 was performed using samples containing either 6.25 μIU/mL (signal) or 0 μIU/mL (blank) of TSH.

| Enhancer | Concentration | Peroxide | Concentration | S/B |
|---|---|---|---|---|
| p-phenylphenol | 8 μM | Urea peroxide | 1 mM | 7.9 |
| p-phenylphenol | 8 μM | Urea peroxide | 2.5 mM | 6.2 |
| p-phenylphenol | 8 μM | Urea peroxide | 5 mM | 7.3 |
| p-phenylphenol | 100 μM | Urea peroxide | 1 mM | 6.0 |
| p-iodophenol | 100 μM | Urea peroxide | 2.5 mM | 8.4 |
| p-phenylphenol | 100 μM | Urea peroxide | 5 mM | 10.6 |

The above data illustrate that various concentrations of enhancer and peroxide can be used in the trigger solutions of the present invention.

Example 33

Investigation of Additional Trigger Solution Compositions

The effectiveness of different trigger solutions was assessed in a model immunoassay system. The protocol of example 20 was performed using samples containing either 6.25 μIU/mL (signal) or 0 μIU/mL (blank) of TSH.

| Enhancer | Concentration | Peroxide | Concentration | S/B |
|---|---|---|---|---|
| p-hydroxycinnamic acid | 8 μM | Urea peroxide | 5 mM | 3.4 |
| d-luciferin | 8 μM | Urea peroxide | 5 mM | 5.7 |
| 6-bromo-2-naphthol | 8 μM | Urea peroxide | 5 mM | 9.6 |
| 2-naphthol | 8 μM | Urea peroxide | 5 mM | 7.5 |
| p-iodophenol | 8 μM | Urea peroxide | 5 mM | 5.3 |
| p-phenylphenol | 8 μM | Urea peroxide | 5 mM | 8.5 |

The above data illustrate that various different enhancers can be used in the trigger solutions of the present invention.

Modification of all of the specific protocols above by use of varying amounts of particles, signal antibody, different incubation conditions, luminescence read times, and additional wash and separation steps can be made without departing from the scope of the present invention.

What is claimed is:

1. A specific binding assay for detecting an analyte in a sample containing or suspected to contain the analyte, the assay comprising:
   a solid support having immobilized thereon a chemiluminescent compound and a first specific binding partner for the analyte; and
   an activator compound conjugate that includes an activator compound conjugated to a second specific binding partner; and
   wherein specific binding of the activator compound conjugate to the analyte bound to the first specific binding partner brings the activator compound conjugate in operable proximity to the immobilized chemiluminescent compound, or wherein specific binding of the activator compound conjugate to the first specific binding partner brings the activator compound conjugate in operable proximity to the immobilized chemiluminescent compound; and
   wherein adding a trigger solution produces chemiluminescence proportional to the amount of the activator compound conjugate in operable proximity to the immobilized chemiluminescent compound for detecting the presence, location, or amount of the analyte in the sample.

2. The assay of claim 1 wherein the activator compound conjugate comprises an activator compound conjugated to a second specific binding partner that binds to the analyte.

3. The assay of claim 1 wherein the activator compound conjugate comprises an activator compound conjugated to an analyte or analyte analog and wherein the amount of chemiluminescence is inversely related to the amount of analyte in the sample.

4. The assay of claim 1 wherein the activator compound is a peroxidase enzyme, wherein the chemiluminescent compound is a substrate for a peroxidase enzyme, and wherein the trigger solution is an aqueous solution comprising a peroxide compound.

5. The assay of claim 1 wherein the activator compound is selected from at least one of transition metal salts and complexes, and transition metal-containing enzymes, wherein the transition metal is selected from at least one of iron, copper, cobalt, zinc, manganese, and chromium, wherein the trigger solution is an aqueous solution comprising a peroxide compound, and wherein the chemiluminescent compound is oxidized to produce chemiluminescence in the presence of the activator compound and the trigger solution.

6. The assay of claim 1 wherein the immobilized first specific binding partner for the analyte is an antibody.

7. The assay of claim 6 that is a sandwich immunoassay.

8. The assay of claim 6 that is a competitive immunoassay.

9. The assay of claim 1 wherein the immobilized first specific binding partner for the analyte is a binding protein.

10. The assay of claim 1 wherein the chemiluminescent compound is covalently attached to the solid support.

11. The assay of claim 1 wherein the chemiluminescent compound is covalently attached to an auxiliary substance that is immobilized on the solid support.

12. The assay of claim 1 wherein the chemiluminescent compound is covalently attached to a specific binding pair member that is immobilized on the solid support.

13. The assay of claim 1 wherein the analyte is a target nucleic acid and wherein the immobilized first specific binding partner is a nucleic acid complementary to a first region of the target nucleic acid and wherein the activator compound conjugate is an activator compound conjugated to a nucleic acid that is complementary to a second region of the target nucleic acid.

14. The assay of claim 1 wherein an excess of the activator compound conjugate is employed so that a portion of the activator compound conjugate remains unbound, and wherein the unbound activator compound conjugate is not removed before adding the trigger solution.

15. The assay of claim 1 wherein the immobilized first specific binding partner is covalently attached to the solid support.

16. The assay of claim 1 wherein the immobilized first specific binding partner is indirectly attached to the solid support.

17. The assay of claim 1 wherein the chemiluminescent compound comprises a chemiluminescent moiety and a linking moiety and wherein the chemiluminescent moiety is selected from aromatic cyclic diacylhydrazides, MCLA, indole acetic acid, isobutyraldehyde, trihydroxyaromatic compounds, xanthene dyes, acridan esters, acridan thioesters, acridan sulfonamides, acridan ketenedithioacetal compounds, acridan compounds of the formula:

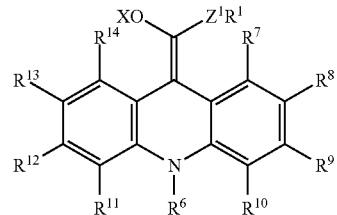

wherein $R^1$ is selected from alkyl, alkenyl, alkynyl, aryl, and aralkyl groups of 1-20 carbon atoms any of which can be substituted with 1-3 groups selected from carbonyl groups, carboxyl groups, tri($C_1$-$C_8$ alkyl)silyl groups, a $SO_3^-$ group, a $OSO_3^{-2}$ group, glycosyl groups, a $PO_3^-$ group, a $OPO_3^{-2}$ group, halogen atoms, a hydroxyl group, a thiol group, amino groups, quaternary ammonium groups, or quaternary phosphonium groups, wherein X is selected from $C_1$-$C_8$ alkyl, aryl, aralkyl groups, alkyl or aryl carboxyl groups having from 1-20 carbon atoms, tri($C_1$-$C_8$ alkyl)silyl groups, a $SO_3^-$ group, glycosyl groups and phosphoryl groups of the formula PO(OR')(OR") wherein R' and R" are independently selected from $C_1$-$C_8$ alkyl, cyanoalkyl, aryl and aralkyl groups, trialkylsilyl groups, alkali metal cations, alkaline earth cations, ammonium and trialkylphosphonium cations, wherein $Z^1$ is selected from O and S atoms, wherein $R^6$ is selected from substituted or unsubstituted $C_1$-$C_4$ alkyl, phenyl, benzyl, alkoxyalkyl and carboxyalkyl groups, wherein 0 or 1 or 2 of the substituents $R^{7-14}$ are selected from alkyl, alkoxy, hydroxy, and halogen and the remaining of $R^{7-14}$ are hydrogen, and compounds of the formula:

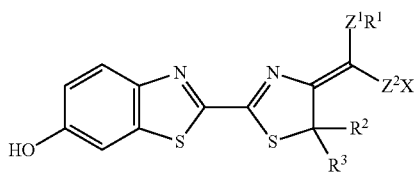

wherein $R^1$ is selected from alkyl, alkenyl, alkynyl, aryl, and aralkyl groups of 1-20 carbon atoms any of which can be substituted with 1-3 groups selected from carbonyl groups, carboxyl groups, tri($C_1$-$C_8$ alkyl)silyl groups, a $SO_3^-$ group, a $OSO_3^{-2}$ group, glycosyl groups, a $PO_3^-$ group, a $OPO_3^{-2}$ group, halogen atoms, a hydroxyl group, a thiol group, amino groups, quaternary ammonium groups, or quaternary phosphonium groups, wherein X is selected from $C_1$-$C_8$ alkyl, aryl, aralkyl groups, alkyl or aryl carboxyl groups having from 1-20 carbon atoms, tri($C_1$-$C_8$ alkyl)silyl groups, a $SO_3^-$ group, glycosyl groups and phosphoryl groups of the formula PO(OR')(OR") wherein R' and R" are independently selected from $C_1$-$C_8$ alkyl, cyanoalkyl, aryl and aralkyl groups, trialkylsilyl groups, alkali metal cations, alkaline earth cations, ammonium and trialkylphosphonium cations, wherein $Z^1$ and $Z^2$ are each selected from O and S atoms and wherein $R^2$ and $R^3$ are independently selected from hydrogen and $C_1$-$C_8$ alkyl.

18. The assay of claim 17 wherein the linking moiety comprises an alkylene chain of 1-20 atoms terminating in a —$CH_2$—, —O—, —S—, —NH—, —NR—, —SiO—, —C(═O)—, —OC(═O)—, —C(═O)O—, —SC(═O)—, —C(═O)S—, —NRC(═O)—, or —C(═O)NR— group, wherein R is $C_{1-8}$ alkyl, or a poly(alkylene-oxy) chain of 3-30 atoms terminating in a —$CH_2$—, —O—, —S—, —NH—, —NR—, —SiO—, —C(═O)—, —OC(═O)—, —C(═O)O—, —SC(═O)—, —C(═O)S—, —NRC(═O)—, or —C(═O)NR— group, wherein R is $C_{1-8}$ alkyl.

19. The assay of claim 1 wherein the solid support is selected from microwell plates, test tubes, sample cups, cellulose test strips, paper test strips, and plastic test strips.

20. The assay of claim 2 wherein the first specific binding partner, the second specific binding partner, or both are antibodies.

21. The assay of claim 2 wherein the first specific binding partner, the second specific binding partner, or both are nucleic acids.

22. The assay of claim 3 wherein the first specific binding partner is an antibody.

23. The assay of claim 3 wherein the first specific binding partner is a nucleic acid.

24. The assay of claim 1 wherein the solid support is selected from plastic spheres, latex particles, polymer particles, silica particles, metal colloids, and magnetic particles.

* * * * *